United States Patent
Bramucci

(10) Patent No.: US 7,045,338 B2
(45) Date of Patent: May 16, 2006

(54) TEMPERATURE SENSITIVE MUTANT DERIVATIVES OF THE BROAD HOST RANGE PLASMID PBHR1

(75) Inventor: Michael G. Bramucci, Folsom, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/378,967

(22) Filed: Mar. 4, 2003

(65) Prior Publication Data

US 2003/0219901 A1    Nov. 27, 2003

Related U.S. Application Data

(60) Provisional application No. 60/362,597, filed on Mar. 8, 2002.

(51) Int. Cl.
*C12N 1/21* (2006.01)
*C12N 15/63* (2006.01)
*C12N 15/11* (2006.01)

(52) U.S. Cl. .......................... 435/252.33; 435/252.34; 435/252.3; 435/320.1; 536/23.1

(58) Field of Classification Search ................ None
See application file for complete search history.

(56) References Cited

U.S. PATENT DOCUMENTS 6,365,410 B1    4/2002    Schellenberger et al.

2002/0119573 A1    8/2002    Shaw et al.

FOREIGN PATENT DOCUMENTS

FR    2690459    10/1993

OTHER PUBLICATIONS

Schmidhauser, T. J. et al., Regions of Broad-Host-Range Plasmid RK2 Involved in Replication and Stable Maintenance in Nine Species of Gram-Negative Bacteria, J. Bacteriol. vol. 164: pp. 446-455, 1985.

Szpiner et al., *Escherichia coli*. GenBank Y14439. Mar. 10, 2001.

Antoine, R. et al., Isolation and molecular characterization of a novel broad-host-range plasmid from Bordetella bronchlseptica with sequence similarities to plasmids from Gram-positive organisms. Mol. Microbiol. vol. 6(13), pp. 1785-1799, 1992.

Szpirer et al., Interaction between the RP4 coupling protein TraG and the pBHR1 mobilization protein Mob. Molecular Microb, 37(6): pp. 1283-1292, 2000.

Szpirer et al., Mobilization Function of the pBHR1 Plasmid, a Derivative of the Broad-Host-Range Plasmid pBBR1, J. Bacteriol. 183(6): 2101-2110, 2001.

*Primary Examiner*—Nancy Vogel

(57) ABSTRACT

The present invention describes a mutant plasmid replication control region having the ability to convey temperature sensitivity to the plasmid on which it resides. The mutant replication control region is based on a similar region isolated from pBRH1. Plasmids containing this rggeplication control region cannot be classed as belonging to any known incompatibility group and thus may co-exist with a broad range of other plasmids in a single host.

9 Claims, 2 Drawing Sheets

SEQUENCE LISTING

```
<160> NUMBER OF SEQ ID NOS: 12

<210> SEQ ID NO 1
<211> LENGTH: 1372
<212> TYPE: DNA
<213> ORGANISM: Escherichia coli
<220> FEATURE:
<221> NAME/KEY: misc_feature
<222> LOCATION: (1)..(1372)
<223> OTHER INFORMATION: Corresponds to nucleotides 2479 to 3851 of
      plasmid pBHR1 (GenbankY14439); "wildtype" sequence
```

<220> FEATURE:
<221> NAME/KEY: exon
<222> LOCATION: (1)..(1372)
<223> OTHER INFORMATION:

<400> SEQUENCE: 1

| | | | | | | | | | | | | | | | | |
|---|---|---|---|---|---|---|---|---|---|---|---|---|---|---|---|---|
| tcg | agc | aag | acg | ttt | ccc | gtt | gaa | tat | ggc | tca | taa | cac | ccc | ttg | tat | 48 |
| Ser | Ser | Lys | Thr | Phe | Pro | Val | Glu | Tyr | Gly | Ser | | His | Pro | Leu | Tyr | |
| 1 | | | | 5 | | | | | 10 | | | | | | 15 | |
| tac | tgt | tta | tgt | aag | cag | aca | gtt | tta | ttg | ttc | atg | atg | ata | tat | ttt | 96 |
| Tyr | Cys | Leu | Cys | Lys | Gln | Thr | Val | Leu | Leu | Phe | Met | Met | Ile | Tyr | Phe | |
| | | | 20 | | | | | 25 | | | | | 30 | | | |
| tat | ctt | gtg | caa | tgt | aac | atc | aga | gat | ttt | gag | aca | caa | cgt | ggc | ttt | 144 |
| Tyr | Leu | Val | Gln | Cys | Asn | Ile | Arg | Asp | Phe | Glu | Thr | Gln | Arg | Gly | Phe | |
| | | | 35 | | | | 40 | | | | | 45 | | | | |
| ccc | ccc | ccc | ccc | tgc | agg | tcc | cga | gcc | tca | cgg | cgg | cga | gtg | cgg | ggg | 192 |
| Pro | Pro | Pro | Pro | Cys | Arg | Ser | Arg | Ala | Ser | Arg | Arg | Arg | Val | Arg | Gly | |
| | 50 | | | | 55 | | | | | 60 | | | | | | |
| ttc | caa | ggg | ggc | agc | gcc | acc | ttg | ggc | aag | gcc | gaa | ggc | cgc | gca | gtc | 240 |
| Phe | Gln | Gly | Gly | Ser | Ala | Thr | Leu | Gly | Lys | Ala | Glu | Gly | Arg | Ala | Val | |
| | 65 | | | | 70 | | | | | 75 | | | | | | |
| gat | caa | caa | gcc | ccg | gag | ggg | cca | ctt | ttt | gcc | gga | ggg | gga | gcc | gcg | 288 |
| Asp | Gln | Gln | Ala | Pro | Glu | Gly | Pro | Leu | Phe | Ala | Gly | Gly | Gly | Ala | Ala | |
| 80 | | | | 85 | | | | | 90 | | | | | 95 | | |
| ccg | aag | gcg | tgg | ggg | aac | ccc | gca | ggg | gtg | ccc | ttc | ttt | ggg | cac | caa | 336 |
| Pro | Lys | Ala | Trp | Gly | Asn | Pro | Ala | Gly | Val | Pro | Phe | Phe | Gly | His | Gln | |
| | | | | 100 | | | | | 105 | | | | | 110 | | |
| aga | act | aga | tat | agg | gcg | aaa | tgc | gaa | aga | ctt | aaa | aat | caa | caa | ctt | 384 |
| Arg | Thr | Arg | Tyr | Arg | Ala | Lys | Cys | Glu | Arg | Leu | Lys | Asn | Gln | Gln | Leu | |
| | | | 115 | | | | | 120 | | | | | 125 | | | |
| aaa | aaa | ggg | ggg | tac | gca | aca | gct | cat | tgc | ggc | acc | ccc | cgc | aat | agc | 432 |
| Lys | Lys | Gly | Gly | Tyr | Ala | Thr | Ala | His | Cys | Gly | Thr | Pro | Arg | Asn | Ser | |
| | | | 130 | | | | | 135 | | | | | 140 | | | |
| tca | ttg | cgt | agg | tta | aag | aaa | atc | tgt | aat | tga | ctg | cca | ctt | tta | cgc | 480 |
| Ser | Leu | Arg | Arg | Leu | Lys | Lys | Ile | Cys | Asn | | Leu | Pro | Leu | Leu | Arg | |
| | 145 | | | | 150 | | | | | | | 155 | | | | |
| aac | gca | taa | ttg | ttg | tcg | cgc | tgc | cga | aaa | gtt | gca | gct | gat | tgc | gca | 528 |
| Asn | Ala | | Leu | Leu | Ser | Arg | Cys | Arg | Lys | Val | Ala | Ala | Asp | Cys | Ala | |
| | 160 | | | | | 165 | | | | | 170 | | | | | |
| tgg | tgc | cgc | aac | cgt | gcg | gca | ccc | tac | cgc | atg | gag | ata | agc | atg | gcc | 576 |
| Trp | Cys | Arg | Asn | Arg | Ala | Ala | Pro | Tyr | Arg | Met | Glu | Ile | Ser | Met | Ala | |
| | 175 | | | | | 180 | | | | | 185 | | | | | |
| acg | cag | tcc | aga | gaa | atc | ggc | att | caa | gcc | aag | aac | aag | ccc | ggt | cac | 624 |
| Thr | Gln | Ser | Arg | Glu | Ile | Gly | Ile | Gln | Ala | Lys | Asn | Lys | Pro | Gly | His | |
| 190 | | | | | 195 | | | | | 200 | | | | | 205 | |
| tgg | gtg | caa | acg | gaa | cgc | aaa | gcg | cat | gag | gcg | tgg | gcc | ggg | ctt | att | 672 |
| Trp | Val | Gln | Thr | Glu | Arg | Lys | Ala | His | Glu | Ala | Trp | Ala | Gly | Leu | Ile | |
| | | | | 210 | | | | | 215 | | | | | 220 | | |
| gcg | agg | aaa | ccc | acg | gcg | gca | atg | ctg | ctg | cat | cac | ctc | gtg | gcg | cag | 720 |
| Ala | Arg | Lys | Pro | Thr | Ala | Ala | Met | Leu | Leu | His | His | Leu | Val | Ala | Gln | |
| | | | | 225 | | | | | 230 | | | | | 235 | | |
| atg | ggc | cac | cag | aac | gcc | gtg | gtc | agc | cag | aag | aca | ctt | tcc | aag | | 768 |
| Met | Gly | His | Gln | Asn | Ala | Val | Val | Ser | Gln | Lys | Thr | Leu | Ser | Lys | | |
| | | | 240 | | | | | 245 | | | | | 250 | | | |
| ctc | atc | gga | cgt | tct | ttg | cgg | acg | gtc | caa | tac | gca | gtc | aag | gac | ttg | 816 |
| Leu | Ile | Gly | Arg | Ser | Leu | Arg | Thr | Val | Gln | Tyr | Ala | Val | Lys | Asp | Leu | |
| | | | 255 | | | | | 260 | | | | | 265 | | | |
| gtg | gcc | gag | cgc | tgg | atc | tcc | gtc | gtg | aag | ctc | aac | ggc | ccc | ggc | acc | 864 |
| Val | Ala | Glu | Arg | Trp | Ile | Ser | Val | Val | Lys | Leu | Asn | Gly | Pro | Gly | Thr | |
| 270 | | | | | 275 | | | | | 280 | | | | | 285 | |

| | | | | | | | | | | | | | | |
|---|---|---|---|---|---|---|---|---|---|---|---|---|---|---|
| gtg | tcg | gcc | tac | gtg | gtc | aat | gac | cgc | gtg | gcg | tgg | ggc | cag | ccc | cgc | 912 |
| Val | Ser | Ala | Tyr | Val | Val | Asn | Asp | Arg | Val | Ala | Trp | Gly | Gln | Pro | Arg |
| | | | 290 | | | | | 295 | | | | | 300 | | |

```
gtg tcg gcc tac gtg gtc aat gac cgc gtg gcg tgg ggc cag ccc cgc       912
Val Ser Ala Tyr Val Val Asn Asp Arg Val Ala Trp Gly Gln Pro Arg
            290                 295                 300 gac cag ttg cgc ctg tcg gtg ttc agt gcc gcc gtg gtg gtt gat cac       960
Asp Gln Leu Arg Leu Ser Val Phe Ser Ala Ala Val Val Val Asp His
            305                 310                 315 gac gac cag gac gaa tcg ctg ttg ggg cat ggc gac ctg cgc cgc atc      1008
Asp Asp Gln Asp Glu Ser Leu Leu Gly His Gly Asp Leu Arg Arg Ile
            320                 325                 330 ccg acc ctg tat ccg ggc gag cag caa cta ccg acc ggc ccc ggc gag      1056
Pro Thr Leu Tyr Pro Gly Glu Gln Gln Leu Pro Thr Gly Pro Gly Glu
            335                 340                 345 gag ccg ccc agc cag ccc ggc att ccg ggc atg gaa cca gac ctg cca      1104
Glu Pro Pro Ser Gln Pro Gly Ile Pro Gly Met Glu Pro Asp Leu Pro
350                 355                 360                 365 gcc ttg acc gaa acg gag gaa tgg gaa cgg cgc ggg cag cag cgc ctg      1152
Ala Leu Thr Glu Thr Glu Glu Trp Glu Arg Arg Gly Gln Gln Arg Leu
            370                 375                 380 ccg atg ccc gat gag ccg tgt ttt ctg gac gat ggc gag ccg ttg gag      1200
Pro Met Pro Asp Glu Pro Cys Phe Leu Asp Asp Gly Glu Pro Leu Glu
            385                 390                 395 ccg ccg aca cgg gtc acg ctg ccg cgc cgg tag cac ttg ggt tgc gca      1248
Pro Pro Thr Arg Val Thr Leu Pro Arg Arg     His Leu Gly Cys Ala
            400                 405                     410 gca acc cgt aag tgc gct gtt cca gac tat cgg ctg tag ccg cct cgc      1296
Ala Thr Arg Lys Cys Ala Val Pro Asp Tyr Arg Leu     Pro Pro Arg
            415                 420                     425 cgc cct ata cct tgt ctg cct ccc cgc gtt gcg tcg cgg tgc atg gag      1344
Arg Pro Ile Pro Cys Leu Pro Pro Arg Val Ala Ser Arg Cys Met Glu
            430                 435                 440 ccg ggc cac ctc gac ctg aat gga agc c                                 1372
Pro Gly His Leu Asp Leu Asn Gly Ser
            445                 450

<210> SEQ ID NO 2
<211> LENGTH: 1372
<212> TYPE: DNA
<213> ORGANISM: Escherichia coli
<220> FEATURE:
<221> NAME/KEY: misc_feature
<222> LOCATION: (1220)..(1220)
<223> OTHER INFORMATION: Mutation from base T to C, as compared to
      wildtype
<220> FEATURE:
<221> NAME/KEY: misc_feature
<222> LOCATION: (1336)..(1336)
<223> OTHER INFORMATION: Mutation from base T to G, as compared to
      wildtype
<220> FEATURE:
<221> NAME/KEY: exon
<222> LOCATION: (1)..(1372)
<223> OTHER INFORMATION:

<400> SEQUENCE: 2 tcg agc aag acg ttt ccc gtt gaa tat ggc tca taa cac ccc ttg tat        48
Ser Ser Lys Thr Phe Pro Val Glu Tyr Gly Ser     His Pro Leu Tyr
1               5                   10                  15 tac tgt tta tgt aag cag aca gtt tta ttg ttc atg atg ata tat ttt        96
Tyr Cys Leu Cys Lys Gln Thr Val Leu Leu Phe Met Met Ile Tyr Phe
                20                  25                  30 tat ctt gtg caa tgt aac atc aga gat ttt gag aca caa cgt ggc ttt       144
Tyr Leu Val Gln Cys Asn Ile Arg Asp Phe Glu Thr Gln Arg Gly Phe
            35                  40                  45 ccc ccc ccc ccc tgc agg tcc cga gcc tca cgg cgg cga gtg cgg ggg       192
```

| | | |
|---|---|---|
| Pro Pro Pro Cys Arg Ser Arg Ala Ser Arg Arg Val Arg Gly<br>50          55          60 | | |
| ttc caa ggg ggc agc gcc acc ttg ggc aag gcc gaa ggc cgc gca gtc<br>Phe Gln Gly Gly Ser Ala Thr Leu Gly Lys Ala Glu Gly Arg Ala Val<br>65          70          75 | | 240 |
| gat caa caa gcc ccg gag ggg cca ctt ttt gcc gga ggg gga gcc gcg<br>Asp Gln Gln Ala Pro Glu Gly Pro Leu Phe Ala Gly Gly Gly Ala Ala<br>80          85          90          95 | | 288 |
| ccg aag gcg tgg ggg aac ccc gca ggg gtg ccc ttc ttt ggg cac caa<br>Pro Lys Ala Trp Gly Asn Pro Ala Gly Val Pro Phe Phe Gly His Gln<br>100          105          110 | | 336 |
| aga act aga tat agg gcg aaa tgc gaa aga ctt aaa aat caa caa ctt<br>Arg Thr Arg Tyr Arg Ala Lys Cys Glu Arg Leu Lys Asn Gln Gln Leu<br>115          120          125 | | 384 |
| aaa aaa ggg ggg tac gca aca gct cat tgc ggc acc ccc cgc aat agc<br>Lys Lys Gly Gly Tyr Ala Thr Ala His Cys Gly Thr Pro Arg Asn Ser<br>130          135          140 | | 432 |
| tca ttg cgt agg tta aag aaa atc tgt aat tga ctg cca ctt tta cgc<br>Ser Leu Arg Arg Leu Lys Lys Ile Cys Asn     Leu Pro Leu Leu Arg<br>145          150          155 | | 480 |
| aac gca taa ttg ttg tcg cgc tgc cga aaa gtt gca gct gat tgc gca<br>Asn Ala     Leu Leu Ser Arg Cys Arg Lys Val Ala Ala Asp Cys Ala<br>160          165          170 | | 528 |
| tgg tgc cgc aac cgt gcg gca ccc tac cgc atg gag ata agc atg gcc<br>Trp Cys Arg Asn Arg Ala Ala Pro Tyr Arg Met Glu Ile Ser Met Ala<br>175          180          185 | | 576 |
| acg cag tcc aga gaa atc ggc att caa gcc aag aac aag ccc ggt cac<br>Thr Gln Ser Arg Glu Ile Gly Ile Gln Ala Lys Asn Lys Pro Gly His<br>190          195          200          205 | | 624 |
| tgg gtg caa acg gaa cgc aaa gcg cat gag gcg tgg gcc ggg ctt att<br>Trp Val Gln Thr Glu Arg Lys Ala His Glu Ala Trp Ala Gly Leu Ile<br>210          215          220 | | 672 |
| gcg agg aaa ccc acg gcg gca atg ctg ctg cat cac ctc gtg gcg cag<br>Ala Arg Lys Pro Thr Ala Ala Met Leu Leu His His Leu Val Ala Gln<br>225          230          235 | | 720 |
| atg ggc cac cag aac gcc gtg gtg gtc agc cag aag aca ctt tcc aag<br>Met Gly His Gln Asn Ala Val Val Val Ser Gln Lys Thr Leu Ser Lys<br>240          245          250 | | 768 |
| ctc atc gga cgt tct ttg cgg acg gtc caa tac gca gtc aag gac ttg<br>Leu Ile Gly Arg Ser Leu Arg Thr Val Gln Tyr Ala Val Lys Asp Leu<br>255          260          265 | | 816 |
| gtg gcc gag cgc tgg atc tcc gtc gtg aag ctc aac ggc ccc ggc acc<br>Val Ala Glu Arg Trp Ile Ser Val Val Lys Leu Asn Gly Pro Gly Thr<br>270          275          280          285 | | 864 |
| gtg tcg gcc tac gtg gtc aat gac cgc gtg gcg tgg ggc cag ccc cgc<br>Val Ser Ala Tyr Val Val Asn Asp Arg Val Ala Trp Gly Gln Pro Arg<br>290          295          300 | | 912 |
| gac cag ttg cgc ctg tcg gtg ttc agt gcc gcc gtg gtg gtt gat cac<br>Asp Gln Leu Arg Leu Ser Val Phe Ser Ala Ala Val Val Val Asp His<br>305          310          315 | | 960 |
| gac gac cag gac gaa tcg ctg ttg ggg cat ggc gac ctg cgc cgc atc<br>Asp Asp Gln Asp Glu Ser Leu Leu Gly His Gly Asp Leu Arg Arg Ile<br>320          325          330 | | 1008 |
| ccg acc ctg tat ccg ggc gag cag caa cta ccg acc ggc ccc ggc gag<br>Pro Thr Leu Tyr Pro Gly Glu Gln Gln Leu Pro Thr Gly Pro Gly Glu<br>335          340          345 | | 1056 |
| gag ccg ccc agc cag ccc ggc att ccg ggc atg gaa cca gac ctg cca<br>Glu Pro Pro Ser Gln Pro Gly Ile Pro Gly Met Glu Pro Asp Leu Pro<br>350          355          360          365 | | 1104 |

-continued

```
gcc ttg acc gaa acg gag gaa tgg gaa cgg cgc ggg cag cag cgc ctg      1152
Ala Leu Thr Glu Thr Glu Glu Trp Glu Arg Arg Gly Gln Gln Arg Leu
            370                 375                 380 ccg atg ccc gat gag ccg tgt ttt ctg gac gat ggc gag ccg ttg gag      1200
Pro Met Pro Asp Glu Pro Cys Phe Leu Asp Asp Gly Glu Pro Leu Glu
        385                 390                 395 ccg ccg aca cgg gtc acg ccg cgc cgg tag cac ttg ggt tgc gca          1248
Pro Pro Thr Arg Val Thr Pro Arg Arg     His Leu Gly Cys Ala
    400                 405                     410 gca acc cgt aag tgc gct gtt cca gac tat cgg ctg tag ccg cct cgc      1296
Ala Thr Arg Lys Cys Ala Val Pro Asp Tyr Arg Leu     Pro Pro Arg
            415                 420                     425 cgc cct ata cct tgt ctg cct ccc cgc gtt gcg tcg cgg ggc atg gag      1344
Arg Pro Ile Pro Cys Leu Pro Pro Arg Val Ala Ser Arg Gly Met Glu
        430                 435                 440 ccg ggc cac ctc gac ctg aat gga agc c                                 1372
Pro Gly His Leu Asp Leu Asn Gly Ser
    445                 450
```

<210> SEQ ID NO 3
<211> LENGTH: 1370
<212> TYPE: DNA
<213> ORGANISM: Escherichia coli
<220> FEATURE:
<221> NAME/KEY: misc_feature
<222> LOCATION: (72)..(72)
<223> OTHER INFORMATION: Mutation from base T to A, as compared to
      wildtype
<220> FEATURE:
<221> NAME/KEY: misc_feature
<222> LOCATION: (538)..(538)
<223> OTHER INFORMATION: Mutation from base A to G, as compared to
      wildtype
<220> FEATURE:
<221> NAME/KEY: misc_feature
<222> LOCATION: (1012)..(1012)
<223> OTHER INFORMATION: Mutation from base A to T, as compared to
      wildtype
<220> FEATURE:
<221> NAME/KEY: misc_feature
<222> LOCATION: (1069)..(1069)
<223> OTHER INFORMATION: Deletion of base C, as compared to wildtype
<220> FEATURE:
<221> NAME/KEY: misc_feature
<222> LOCATION: (1155)..(1155)
<223> OTHER INFORMATION: Mutation of base G to C, as compared to
      wildtype
<220> FEATURE:
<221> NAME/KEY: misc_feature
<222> LOCATION: (1220)..(1220)
<223> OTHER INFORMATION: Mutation of base T to C, as compared to
      wildtype
<220> FEATURE:
<221> NAME/KEY: misc_feature
<222> LOCATION: (1243)..(1243)
<223> OTHER INFORMATION: Mutation of base T to C, as compared to
      wildtype
<220> FEATURE:
<221> NAME/KEY: misc_feature
<222> LOCATION: (1271)..(1271)
<223> OTHER INFORMATION: Deletion of base C, as compared to wildtype
<220> FEATURE:
<221> NAME/KEY: exon
<222> LOCATION: (1)..(1370)
<223> OTHER INFORMATION:

<400> SEQUENCE: 3

```
tcg agc aag acg ttt ccc gtt gaa tat ggc tca taa cac ccc ttg tat       48
Ser Ser Lys Thr Phe Pro Val Glu Tyr Gly Ser     His Pro Leu Tyr
1               5                   10                  15 tac tgt tta tgt aag cag aca gta tta ttg ttc atg atg ata tat ttt       96
```

-continued

| | |
|---|---|
| Tyr Cys Leu Cys Lys Gln Thr Val Leu Leu Phe Met Met Ile Tyr Phe<br>             20                       25                 30 | |
| tat ctt gtg caa tgt aac atc aga gat ttt gag aca caa cgt ggc ttt<br>Tyr Leu Val Gln Cys Asn Ile Arg Asp Phe Glu Thr Gln Arg Gly Phe<br>          35                      40                      45 | 144 |
| ccc ccc ccc ccc tgc agg tcc cga gcc tca cgg cgg cga gtg cgg ggg<br>Pro Pro Pro Pro Cys Arg Ser Arg Ala Ser Arg Arg Arg Val Arg Gly<br>          50                      55                      60 | 192 |
| ttc caa ggg ggc agc gcc acc ttg ggc aag gcc gaa ggc cgc gca gtc<br>Phe Gln Gly Gly Ser Ala Thr Leu Gly Lys Ala Glu Gly Arg Ala Val<br>65                      70                      75 | 240 |
| gat caa caa gcc ccg gag ggg cca ctt ttt gcc gga ggg gga gcc gcg<br>Asp Gln Gln Ala Pro Glu Gly Pro Leu Phe Ala Gly Gly Gly Ala Ala<br>80                      85                      90                      95 | 288 |
| ccg aag gcg tgg ggg aac ccc gca ggg gtg ccc ttc ttt ggg cac caa<br>Pro Lys Ala Trp Gly Asn Pro Ala Gly Val Pro Phe Phe Gly His Gln<br>                  100                      105                      110 | 336 |
| aga act aga tat agg gcg aaa tgc gaa aga ctt aaa aat caa caa ctt<br>Arg Thr Arg Tyr Arg Ala Lys Cys Glu Arg Leu Lys Asn Gln Gln Leu<br>                  115                      120                      125 | 384 |
| aaa aaa ggg ggg tac gca aca gct cat tgc ggc acc ccc cgc aat agc<br>Lys Lys Gly Gly Tyr Ala Thr Ala His Cys Gly Thr Pro Arg Asn Ser<br>                  130                      135                      140 | 432 |
| tca ttg cgt agg tta aag aaa atc tgt aat tga ctg cca ctt tta cgc<br>Ser Leu Arg Arg Leu Lys Lys Ile Cys Asn     Leu Pro Leu Leu Arg<br>          145                      150                              155 | 480 |
| aac gca taa ttg ttg tcg cgc tgc cga aaa gtt gca gct gat tgc gca<br>Asn Ala    Leu Leu Ser Arg Cys Arg Lys Val Ala Ala Asp Cys Ala<br>     160                                165                      170 | 528 |
| tgg tgc cgc gac cgt gcg gca ccc tac cgc atg gag ata agc atg gcc<br>Trp Cys Arg Asp Arg Ala Ala Pro Tyr Arg Met Glu Ile Ser Met Ala<br>         175                      180                      185 | 576 |
| acg cag tcc aga gaa atc ggc att caa gcc aag aac aag ccc ggt cac<br>Thr Gln Ser Arg Glu Ile Gly Ile Gln Ala Lys Asn Lys Pro Gly His<br>190                      195                      200                      205 | 624 |
| tgg gtg caa acg gaa cgc aaa gcg cat gag gcg tgg gcc ggg ctt att<br>Trp Val Gln Thr Glu Arg Lys Ala His Glu Ala Trp Ala Gly Leu Ile<br>                  210                      215                      220 | 672 |
| gcg agg aaa ccc acg gcg gca atg ctg ctg cat cac ctc gtg gcg cag<br>Ala Arg Lys Pro Thr Ala Ala Met Leu Leu His His Leu Val Ala Gln<br>         225                      230                      235 | 720 |
| atg ggc cac cag aac gcc gtg gtg gtc agc cag aag aca ctt tcc aag<br>Met Gly His Gln Asn Ala Val Val Val Ser Gln Lys Thr Leu Ser Lys<br>240                      245                      250 | 768 |
| ctc atc gga cgt tct ttg cgg acg gtc caa tac gca gtc aag gac ttg<br>Leu Ile Gly Arg Ser Leu Arg Thr Val Gln Tyr Ala Val Lys Asp Leu<br>         255                      260                      265 | 816 |
| gtg gcc gag cgc tgg atc tcc gtc gtg aag ctc aac ggc ccc ggc acc<br>Val Ala Glu Arg Trp Ile Ser Val Val Lys Leu Asn Gly Pro Gly Thr<br>270                      275                      280                      285 | 864 |
| gtg tcg gcc tac gtg gtc aat gac cgc gtg gcg tgg ggc cag ccc cgc<br>Val Ser Ala Tyr Val Val Asn Asp Arg Val Ala Trp Gly Gln Pro Arg<br>                  290                      295                      300 | 912 |
| gac cag ttg cgc ctg tcg gtg ttc agt gcc gcc gtg gtg gtt gat cac<br>Asp Gln Leu Arg Leu Ser Val Phe Ser Ala Ala Val Val Val Asp His<br>         305                      310                      315 | 960 |
| gac gac cag gac gaa tcg ctg ttg ggg cat ggc gac ctg cgc cgc atc<br>Asp Asp Gln Asp Glu Ser Leu Leu Gly His Gly Asp Leu Arg Arg Ile<br>320                      325                      330 | 1008 |

-continued

```
ccg tcc ctg tat ccg ggc gag cag caa cta ccg acc ggc ccc ggc gag      1056
Pro Ser Leu Tyr Pro Gly Glu Gln Gln Leu Pro Thr Gly Pro Gly Glu
        335                 340                 345 gag ccg ccc agc agc ccg gca ttc cgg gca tgg aac cag acc tgc cag      1104
Glu Pro Pro Ser Ser Pro Ala Phe Arg Ala Trp Asn Gln Thr Cys Gln
350                 355                 360                 365 cct tga ccg aaa cgg agg aat ggg aac ggc gcg ggc agc agc gcc tgc      1152
Pro     Pro Lys Arg Arg Asn Gly Asn Gly Ala Gly Ser Ser Ala Cys
                        370                 375                 380 cca tgc ccg atg agc cgt gtt ttc tgg acg atg gca agc cgt tgg agc      1200
Pro Cys Pro Met Ser Arg Val Phe Trp Thr Met Ala Ser Arg Trp Ser
                385                 390                 395 cgc cga cac ggg tca cgc cgc cgc gcc ggt agc act tgg gtc gcg cag      1248
Arg Arg His Gly Ser Arg Arg Arg Ala Gly Ser Thr Trp Val Ala Gln
            400                 405                 410 caa ccc gta agt gcg ctg ttc aga cta tcg gct gta gcc gcc tcg ccg      1296
Gln Pro Val Ser Ala Leu Phe Arg Leu Ser Ala Val Ala Ala Ser Pro
        415                 420                 425 ccc tat acc ttg tct gcc tcc ccg cgt tgc gtc gcg gtg cat gga gcc      1344
Pro Tyr Thr Leu Ser Ala Ser Pro Arg Cys Val Ala Val His Gly Ala
    430                 435                 440 ggg cca cct cga cct gaa tgg aag cc                                   1370
Gly Pro Pro Arg Pro Glu Trp Lys
445                 450

<210> SEQ ID NO 4
<211> LENGTH: 1372
<212> TYPE: DNA
<213> ORGANISM: Escherichia coli
<220> FEATURE:
<221> NAME/KEY: misc_feature
<222> LOCATION: (1094)..(1094)
<223> OTHER INFORMATION: Mutation from base C to G, as compared to
      wildtype
<220> FEATURE:
<221> NAME/KEY: exon
<222> LOCATION: (1)..(1372)
<223> OTHER INFORMATION:

<400> SEQUENCE: 4 tcg agc aag acg ttt ccc gtt gaa tat ggc tca taa cac ccc ttg tat      48
Ser Ser Lys Thr Phe Pro Val Glu Tyr Gly Ser     His Pro Leu Tyr
1               5                   10                      15 tac tgt tta tgt aag cag aca gtt tta ttg ttc atg atg ata tat ttt      96
Tyr Cys Leu Cys Lys Gln Thr Val Leu Leu Phe Met Met Ile Tyr Phe
            20                  25                  30 tat ctt gtg caa tgt aac atc aga gat ttt gag aca caa cgt ggc ttt      144
Tyr Leu Val Gln Cys Asn Ile Arg Asp Phe Glu Thr Gln Arg Gly Phe
        35                  40                  45 ccc ccc ccc ccc tgc agg tcc cga gcc tca cgg cgg cga gtg cgg ggg      192
Pro Pro Pro Pro Cys Arg Ser Arg Ala Ser Arg Arg Arg Val Arg Gly
    50                  55                  60 ttc caa ggg ggc agc gcc acc ttg ggc aag gcc gaa ggc cgc gca gtc      240
Phe Gln Gly Gly Ser Ala Thr Leu Gly Lys Ala Glu Gly Arg Ala Val
65                  70                  75 gat caa caa gcc ccg gag ggg cca ctt ttt gcc gga ggg gga gcc gcg      288
Asp Gln Gln Ala Pro Glu Gly Pro Leu Phe Ala Gly Gly Gly Ala Ala
80                  85                  90                  95 ccg aag gcg tgg ggg aac ccc gca ggg gtg ccc ttc ttt ggg cac caa      336
Pro Lys Ala Trp Gly Asn Pro Ala Gly Val Pro Phe Phe Gly His Gln
                100                 105                 110 aga act aga tat agg gcg aaa tgc gaa aga ctt aaa aat caa caa ctt      384
Arg Thr Arg Tyr Arg Ala Lys Cys Glu Arg Leu Lys Asn Gln Gln Leu
```

```
                115                 120                 125
aaa aaa ggg ggg tac gca aca gct cat tgc ggc acc ccc cgc aat agc      432
Lys Lys Gly Gly Tyr Ala Thr Ala His Cys Gly Thr Pro Arg Asn Ser
            130                 135                 140 tca ttg cgt agg tta aag aaa atc tgt aat tga ctg cca ctt tta cgc      480
Ser Leu Arg Arg Leu Lys Lys Ile Cys Asn     Leu Pro Leu Leu Arg
145                 150                 155 aac gca taa ttg ttg tcg cgc tgc cga aaa gtt gca gct gat tgc gca      528
Asn Ala     Leu Leu Ser Arg Cys Arg Lys Val Ala Ala Asp Cys Ala
    160                 165                 170 tgg tgc cgc aac cgt gcg gca ccc tac cgc atg gag ata agc atg gcc      576
Trp Cys Arg Asn Arg Ala Ala Pro Tyr Arg Met Glu Ile Ser Met Ala
175                 180                 185 acg cag tcc aga gaa atc ggc att caa gcc aag aac aag ccc ggt cac      624
Thr Gln Ser Arg Glu Ile Gly Ile Gln Ala Lys Asn Lys Pro Gly His
190                 195                 200                 205 tgg gtg caa acg gaa cgc aaa gcg cat gag gcg tgg gcc ggg ctt att      672
Trp Val Gln Thr Glu Arg Lys Ala His Glu Ala Trp Ala Gly Leu Ile
                210                 215                 220 gcg agg aaa ccc acg gcg gca atg ctg ctg cat cac ctc gtg gcg cag      720
Ala Arg Lys Pro Thr Ala Ala Met Leu Leu His His Leu Val Ala Gln
            225                 230                 235 atg ggc cac cag aac gcc gtg gtg gtc agc cag aag aca ctt tcc aag      768
Met Gly His Gln Asn Ala Val Val Val Ser Gln Lys Thr Leu Ser Lys
        240                 245                 250 ctc atc gga cgt tct ttg cgg acg gtc caa tac gca gtc aag gac ttg      816
Leu Ile Gly Arg Ser Leu Arg Thr Val Gln Tyr Ala Val Lys Asp Leu
    255                 260                 265 gtg gcc gag cgc tgg atc tcc gtc gtg aag ctc aac ggc ccc ggc acc      864
Val Ala Glu Arg Trp Ile Ser Val Val Lys Leu Asn Gly Pro Gly Thr
270                 275                 280                 285 gtg tcg gcc tac gtg gtc aat gac cgc gtg gcg tgg ggc cag ccc cgc      912
Val Ser Ala Tyr Val Val Asn Asp Arg Val Ala Trp Gly Gln Pro Arg
                290                 295                 300 gac cag ttg cgc ctg tcg gtg ttc agt gcc gcc gtg gtg gtt gat cac      960
Asp Gln Leu Arg Leu Ser Val Phe Ser Ala Ala Val Val Val Asp His
            305                 310                 315 gac gac cag gac gaa tcg ctg ttg ggg cat ggc gac ctg cgc cgc atc     1008
Asp Asp Gln Asp Glu Ser Leu Leu Gly His Gly Asp Leu Arg Arg Ile
        320                 325                 330 ccg acc ctg tat ccg ggc gag cag caa cta ccg acc ggc ccc ggc gag     1056
Pro Thr Leu Tyr Pro Gly Glu Gln Gln Leu Pro Thr Gly Pro Gly Glu
    335                 340                 345 gag ccg ccc agc cag ccc ggc att ccg ggc atg gaa cga gac ctg cca     1104
Glu Pro Pro Ser Gln Pro Gly Ile Pro Gly Met Glu Arg Asp Leu Pro
350                 355                 360                 365 gcc ttg acc gaa acg gag gaa tgg gaa cgg cgc ggg cag cag cgc ctg     1152
Ala Leu Thr Glu Thr Glu Glu Trp Glu Arg Arg Gly Gln Gln Arg Leu
                370                 375                 380 ccg atg ccc gat gag ccg tgt ttt ctg gac gat ggc gag ccg ttg gag     1200
Pro Met Pro Asp Glu Pro Cys Phe Leu Asp Asp Gly Glu Pro Leu Glu
            385                 390                 395 ccg ccg aca cgg gtc acg ctg ccg cgc cgg tag cac ttg ggt tgc gca     1248
Pro Pro Thr Arg Val Thr Leu Pro Arg Arg     His Leu Gly Cys Ala
        400                 405                         410 gca acc cgt aag tgc gct gtt cca gac tat cgg ctg tag ccg cct cgc     1296
Ala Thr Arg Lys Cys Ala Val Pro Asp Tyr Arg Leu     Pro Pro Arg
    415                 420                         425 cgc cct ata cct tgt ctg cct ccc cgc gtt gcg tcg cgg tgc atg gag     1344
```

```
Arg Pro Ile Pro Cys Leu Pro Pro Arg Val Ala Ser Arg Cys Met Glu
        430                 435                 440 ccg ggc cac ctc gac ctg aat gga agc c                              1372
Pro Gly His Leu Asp Leu Asn Gly Ser
        445                 450

<210> SEQ ID NO 5
<211> LENGTH: 1372
<212> TYPE: DNA
<213> ORGANISM: Escherichia coli
<220> FEATURE:
<221> NAME/KEY: misc_feature
<222> LOCATION: (412)..(412)
<223> OTHER INFORMATION: Mutation from base T to C, as compared to
      wildtype
<220> FEATURE:
<221> NAME/KEY: exon
<222> LOCATION: (1)..(1372)
<223> OTHER INFORMATION:

<400> SEQUENCE: 5 tcg agc aag acg ttt ccc gtt gaa tat ggc tca taa cac ccc ttg tat     48
Ser Ser Lys Thr Phe Pro Val Glu Tyr Gly Ser     His Pro Leu Tyr
1                5                  10                      15 tac tgt tta tgt aag cag aca gtt tta ttg ttc atg atg ata tat ttt     96
Tyr Cys Leu Cys Lys Gln Thr Val Leu Leu Phe Met Met Ile Tyr Phe
                20                  25                  30 tat ctt gtg caa tgt aac atc aga gat ttt gag aca caa cgt ggc ttt    144
Tyr Leu Val Gln Cys Asn Ile Arg Asp Phe Glu Thr Gln Arg Gly Phe
            35                  40                  45 ccc ccc ccc ccc tgc agg tcc cga gcc tca cgg cgg cga gtg cgg ggg    192
Pro Pro Pro Pro Cys Arg Ser Arg Ala Ser Arg Arg Arg Val Arg Gly
        50                  55                  60 ttc caa ggg ggc agc gcc acc ttg ggc aag gcc gaa ggc cgc gca gtc    240
Phe Gln Gly Gly Ser Ala Thr Leu Gly Lys Ala Glu Gly Arg Ala Val
65                  70                  75 gat caa caa gcc ccg gag ggg cca ctt ttt gcc gga ggg gga gcc gcg    288
Asp Gln Gln Ala Pro Glu Gly Pro Leu Phe Ala Gly Gly Gly Ala Ala
80                  85                  90                  95 ccg aag gcg tgg ggg aac ccc gca ggg gtg ccc ttc ttt ggg cac caa    336
Pro Lys Ala Trp Gly Asn Pro Ala Gly Val Pro Phe Phe Gly His Gln
            100                 105                 110 aga act aga tat agg gcg aaa tgc gaa aga ctt aaa aat caa caa ctt    384
Arg Thr Arg Tyr Arg Ala Lys Cys Glu Arg Leu Lys Asn Gln Gln Leu
        115                 120                 125 aaa aaa ggg ggg tac gca aca gct cat cgc ggc acc ccc cgc aat agc    432
Lys Lys Gly Gly Tyr Ala Thr Ala His Arg Gly Thr Pro Arg Asn Ser
    130                 135                 140 tca ttg cgt agg tta aag aaa atc tgt aat tga ctg cca ctt tta cgc    480
Ser Leu Arg Arg Leu Lys Lys Ile Cys Asn     Leu Pro Leu Leu Arg
145                 150                 155 aac gca taa ttg ttg tcg cgc tgc cga aaa gtt gca gct gat tgc gca    528
Asn Ala     Leu Leu Ser Arg Cys Arg Lys Val Ala Ala Asp Cys Ala
    160                 165                 170 tgg tgc cgc aac cgt gcg gca ccc tac cgc atg gag ata agc atg gcc    576
Trp Cys Arg Asn Arg Ala Ala Pro Tyr Arg Met Glu Ile Ser Met Ala
175                 180                 185 acg cag tcc aga gaa atc ggc att caa gcc aag aac aag ccc ggt cac    624
Thr Gln Ser Arg Glu Ile Gly Ile Gln Ala Lys Asn Lys Pro Gly His
190                 195                 200                 205 tgg gtg caa acg gaa cgc aaa gcg cat gag gcg tgg gcc ggg ctt att    672
Trp Val Gln Thr Glu Arg Lys Ala His Glu Ala Trp Ala Gly Leu Ile
            210                 215                 220
```

```
gcg agg aaa ccc acg gcg gca atg ctg ctg cat cac ctc gtg gcg cag      720
Ala Arg Lys Pro Thr Ala Ala Met Leu Leu His His Leu Val Ala Gln
        225                 230                 235 atg ggc cac cag aac gcc gtg gtg gtc agc cag aag aca ctt tcc aag      768
Met Gly His Gln Asn Ala Val Val Val Ser Gln Lys Thr Leu Ser Lys
                240                 245                 250 ctc atc gga cgt tct ttg cgg acg gtc caa tac gca gtc aag gac ttg      816
Leu Ile Gly Arg Ser Leu Arg Thr Val Gln Tyr Ala Val Lys Asp Leu
        255                 260                 265 gtg gcc gag cgc tgg atc tcc gtc gtg aag ctc aac ggc ccc ggc acc      864
Val Ala Glu Arg Trp Ile Ser Val Val Lys Leu Asn Gly Pro Gly Thr
270                 275                 280                 285 gtg tcg gcc tac gtg gtc aat gac cgc gtg gcg tgg ggc cag ccc cgc      912
Val Ser Ala Tyr Val Val Asn Asp Arg Val Ala Trp Gly Gln Pro Arg
                290                 295                 300 gac cag ttg cgc ctg tcg gtg ttc agt gcc gcc gtg gtg gtt gat cac      960
Asp Gln Leu Arg Leu Ser Val Phe Ser Ala Ala Val Val Val Asp His
        305                 310                 315 gac gac cag gac gaa tcg ctg ttg ggg cat ggc gac ctg cgc cgc atc     1008
Asp Asp Gln Asp Glu Ser Leu Leu Gly His Gly Asp Leu Arg Arg Ile
                320                 325                 330 ccg acc ctg tat ccg ggc gag cag caa cta ccg acc ggc ccc ggc gag     1056
Pro Thr Leu Tyr Pro Gly Glu Gln Gln Leu Pro Thr Gly Pro Gly Glu
        335                 340                 345 gag ccg ccc agc cag ccc ggc att ccg ggc atg gaa cca gac ctg cca     1104
Glu Pro Pro Ser Gln Pro Gly Ile Pro Gly Met Glu Pro Asp Leu Pro
350                 355                 360                 365 gcc ttg acc gaa acg gag gaa tgg gaa cgg cgc ggg cag cag cgc ctg     1152
Ala Leu Thr Glu Thr Glu Glu Trp Glu Arg Arg Gly Gln Gln Arg Leu
                370                 375                 380 ccg atg ccc gat gag ccg tgt ttt ctg gac gat ggc gag ccg ttg gag     1200
Pro Met Pro Asp Glu Pro Cys Phe Leu Asp Asp Gly Glu Pro Leu Glu
        385                 390                 395 ccg ccg aca cgg gtc acg ctg ccg cgc cgg tag cac ttg ggt tgc gca     1248
Pro Pro Thr Arg Val Thr Leu Pro Arg Arg     His Leu Gly Cys Ala
                400                 405                 410 gca acc cgt aag tgc gct gtt cca gac tat cgg ctg tag ccg cct cgc     1296
Ala Thr Arg Lys Cys Ala Val Pro Asp Tyr Arg Leu     Pro Pro Arg
        415                 420                         425 cgc cct ata cct tgt ctg cct ccc cgc gtt gcg tcg cgg tgc atg gag     1344
Arg Pro Ile Pro Cys Leu Pro Pro Arg Val Ala Ser Arg Cys Met Glu
                430                 435                 440 ccg ggc cac ctc gac ctg aat gga agc c                                1372
Pro Gly His Leu Asp Leu Asn Gly Ser
        445                 450

<210> SEQ ID NO 6
<211> LENGTH: 675
<212> TYPE: DNA
<213> ORGANISM: Escherichia coli
<220> FEATURE:
<221> NAME/KEY: exon
<222> LOCATION: (1)..(675)
<223> OTHER INFORMATION:

<400> SEQUENCE: 6 atg gag ata agc atg gcc acg cag tcc aga gaa atc ggc att caa gcc       48
Met Glu Ile Ser Met Ala Thr Gln Ser Arg Glu Ile Gly Ile Gln Ala
1               5                   10                  15 aag aac aag ccc ggt cac tgg gtg caa acg gaa cgc aaa gcg cat gag       96
Lys Asn Lys Pro Gly His Trp Val Gln Thr Glu Arg Lys Ala His Glu
```

-continued

```
                    20                  25                  30
gcg tgg gcc ggg ctt att gcg agg aaa ccc acg gcg gca atg ctg ctg      144
Ala Trp Ala Gly Leu Ile Ala Arg Lys Pro Thr Ala Ala Met Leu Leu
         35                  40                  45 cat cac ctc gtg gcg cag atg ggc cac cag aac gcc gtg gtg gtc agc      192
His His Leu Val Ala Gln Met Gly His Gln Asn Ala Val Val Val Ser
 50                  55                  60 cag aag aca ctt tcc aag ctc atc gga cgt tct ttg cgg acg gtc caa      240
Gln Lys Thr Leu Ser Lys Leu Ile Gly Arg Ser Leu Arg Thr Val Gln
 65                  70                  75                  80 tac gca gtc aag gac ttg gtg gcc gag cgc tgg atc tcc gtc gtg aag      288
Tyr Ala Val Lys Asp Leu Val Ala Glu Arg Trp Ile Ser Val Val Lys
                 85                  90                  95 ctc aac ggc ccc ggc acc gtg tcg gcc tac gtg gtc aat gac cgc gtg      336
Leu Asn Gly Pro Gly Thr Val Ser Ala Tyr Val Val Asn Asp Arg Val
            100                 105                 110 gcg tgg ggc cag ccc cgc gac cag ttg cgc ctg tcg gtg ttc agt gcc      384
Ala Trp Gly Gln Pro Arg Asp Gln Leu Arg Leu Ser Val Phe Ser Ala
        115                 120                 125 gcc gtg gtg gtt gat cac gac gac cag gac gaa tcg ctg ttg ggg cat      432
Ala Val Val Val Asp His Asp Asp Gln Asp Glu Ser Leu Leu Gly His
    130                 135                 140 ggc gac ctg cgc cgc atc ccg wcc ctg tat ccg ggc gag cag caa cta      480
Gly Asp Leu Arg Arg Ile Pro Xaa Leu Tyr Pro Gly Glu Gln Gln Leu
145                 150                 155                 160 ccg acc ggc ccc ggc gag gag ccg ccc agc cag ccc ggc att ccg ggc      528
Pro Thr Gly Pro Gly Glu Glu Pro Pro Ser Gln Pro Gly Ile Pro Gly
                165                 170                 175 atg gaa csa gac ctg cca gcc ttg acc gaa acg gag gaa tgg gaa cgg      576
Met Glu Xaa Asp Leu Pro Ala Leu Thr Glu Thr Glu Glu Trp Glu Arg
            180                 185                 190 cgc ggg cag cag cgc ctg ccs atg ccc gat gag ccg tgt ttt ctg gac      624
Arg Gly Gln Gln Arg Leu Xaa Met Pro Asp Glu Pro Cys Phe Leu Asp
        195                 200                 205 gat ggc gag ccg ttg gag ccg ccg aca cgg gtc acg cyg ccg cgc cgg      672
Asp Gly Glu Pro Leu Glu Pro Pro Thr Arg Val Thr Xaa Pro Arg Arg
    210                 215                 220 tag                                                                   675
```

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ctgaccatct catctgtaac                                                  20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
caaatgcctg aggccagttt g                                                21

<210> SEQ ID NO 9
<211> LENGTH: 20

```
<212> TYPE: DNA
<213> ORGANISM: Artificial Sequence
<220> FEATURE:
<223> OTHER INFORMATION: Primer

<400> SEQUENCE: 9
tctttgggca ccaaagaact                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcctgtcggt gttcagtgcc                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gccgacacgg tgccggggcc                                              20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gcaaaaagtg gccctccgg                                               20
```

TEMPERATURE SENSITIVE MUTANT DERIVATIVES OF THE BROAD HOST RANGE PLASMID PBHR1

This application claims the benefit of U.S. Provisional Application No. 60/362,597, filed Mar. 8, 2002.

FIELD OF INVENTION

The present invention relates to the field of molecular biology and cloning vectors. More specifically, the present invention relates to temperature-sensitive broad host range plasmids derived from pBHR1.

BACKGROUND OF THE INVENTION

Bacterial plasmids are extrachromosomal DNA molecules that replicate autonomously in the host cell. They vary in size from one to several hundred kilobases (kB) and in copy number from one to several hundred per cell. However, not all plasmids are inherently useful for a molecular biologist to use as a cloning vector. Desirable characteristics of a cloning vector include: 1.) small size (i.e., less than about 6 kB); 2.) relatively high copy number; 3.) presence of a selectable marker; and 4.) presence of single sites for cleavage by restriction enzymes.

Applications using non-enteric bacteria for basic and applied molecular research have extended the criteria one must consider with respect to choice of a plasmid cloning vector. Specifically, host range refers to the types of microbes in which a plasmid will replicate. One may develop a specific vector for each microbial species of interest, or one may take advantage of available broad host range replicons which have the ability to be maintained in a wide range of microbes that are unrelated. These broad host range plasmids typically encode all of their own proteins required for replication initiation, and therefore are not dependent on their host cell. In contrast, narrow host range replicons may lack replication or segregation proficiencies (as compared to an inability to be introduced into or express genetic markers in a distantly related host), which result in their replication only in closely related species (Schmidhauser, T. J. and D. R. Helinski. *J. Bacteriol.* 164:446–455 (1985)). Most broad host range plasmids are classified on the basis of their intrinsic properties, according to their "incompatibility groups". This classification reflects the similarities in sequence, function, and the nature of the replicon (as replicons of the same type are unable to co-exist in a cell, while replicons from different incompatibility groups (e.g., "Inc" groups) may exist simultaneously in a single cell). Natural plasmid isolates of gram-negative bacteria that belong to incompatibility groups C, N, P, Q and W display replication and maintenance proficiency in a diversity of bacterial species.

A particularly useful broad host range plasmid is the commercially available pBHR1 (MoBiTec; Göttingen, Germany; GenBank Y14439). This plasmid was derived from the broad host range plasmid pBBR1, which was isolated from the gram-negative bacterium *Bordetella bronchiseptica* S87 (Antoine, R. and C. Locht, *Mol. Microbiol.* 6(13): 1785–1799 (1992); FR 2,690,459). Like pBBR1, pBHR1 does not belong to any of the common broad host range incompatibility groups and possesses a relatively high copy number. Both plasmids possess two critical open reading frames (ORFs)—the first, known as rep, is involved in replication of the plasmid; and the second ORF is known as mob. The mob gene, involved in mobilization, has been extensively characterized for this family of plasmids by Szpirer et al. (*Molecular Microb.* 37(6): 1283–1292 (2000); *J. Bacteriol.* 183(6): 2101–2110 (2001)). Plasmid pBHR1 also additionally has two selectable markers (kanamycin and chloramphenicol), while maintaining a relatively small size of only 5300 bp. These properties render pBHR1 as an extremely useful cloning vector suitable for a wide range of gram-negative bacteria.

One variation that would increase the utility of pBHR1 would be creation of a temperature sensitive (Ts) mutant, such that it would be possible to control when the plasmid replicated within the host cell. Temperature sensitive mutants typically express their mutant phenotypes at elevated temperatures. Ideally, the replication Ts mutant of pBHR1 would grow and replicate normally at the permissive temperature, but the mutant phenotype (i.e., a non-replicative plasmid) would only be expressed at the elevated, or "restrictive", temperature in a conditional manner. Growth of the bacterial host under these restrictive conditions would result in plasmid elimination or integration of the plasmid into the chromosome at regions of significant DNA homology. Thus, a Ts-pBHR1 plasmid would be useful for: 1.) plasmid curing (whereby it is desirable to eliminate a plasmid from a bacterial strain); 2.) plasmid chasing (whereby it is possible to remove, or "chase", other plasmids from a bacterial strain that are incompatible with the subsequently introduced plasmid); and 3.) the creation of single and double crossover mutants by homologous recombination (whereby a particular region of DNA can be integrated into a host chromosome from a plasmid). It is especially desirable to have an effective means available for introducing or specifically and permanently modifying certain genes in microbial host organisms.

Temperature sensitive mutants are generated by random mutagenesis followed by screening to obtain mutants with a Ts phenotype. Although the technique of generating these mutants is well understood by an artisan skilled in molecular biology, the tremendous utility and need for development of a Ts-pBHR1 plasmid has not previously been recognized. Furthermore, it is impossible to predict which mutations in the replication control region of pBHR1 will encode temperature sensitive mutations.

The problem to be solved therefore is to develop a temperature sensitive broad host range plasmid having the ability to co-exist with a variety of other broad host range plasmids.

Applicants have solved the stated problem by isolating a suite of temperature sensitive plasmids derived from pBHR1, containing mutant replication control regions. The broad host range of the plasmid, and its compatibility with other known broad host range vectors, makes the Ts-plasmid of the present invention particularly attractive for the genetic engineering of non-enteric bacteria for basic and applied molecular research.

SUMMARY OF THE INVENTION

The present invention provides a mutant replication control region of a plasmid having the ability to convey temperature sensitivity to a plasmid on which it resides. Also provided are plasmids comprising the mutant replication control region. Because they are not members of standard incompatibility groups the plasmids of the invention are additionally compatible with a wide variety of other plasmids, thereby providing a method for efficiently modifying genetic traits of a host in a short period of time.

Several mutations have been identified in plasmid pBHR1 that permit its autonomous replication at a permissive temperature but that do not permit its autonomous replication at a restrictive temperature. These mutations of the replication control region include, but are not limited to those located at positions 72, 412, 538, 1012, 1069, 1094, 1155, 1220, 1243, 1271, and 1336 of the nucleotide sequence of the replication control region of pBHR1.

Accordingly the invention provides a method for the generation and isolation of a temperature sensitive mutant plasmid replication control region comprising:
 a) providing a pBHR1 plasmid;
 b) subjecting the plasmid of (a) to a mutagenic procedure wherein mutations are introduced into the replication control region of the pBHR1 plasmid;
 c) culturing the mutagenized plasmid of (b) at a permissive temperature;
 d) selecting at least one plasmid of (c) which does not replicate at a restrictive temperature; and
 e) isolating mutant replication control regions from the plasmids of (d).

In another embodiment the invention provides a mutant replication region having a nucleotide sequence as set forth in SEQ ID NO:1 and having at least one point mutation independently selected from the group consisting of:
 a) a mutation of T to A at nucleotide number 72,
 b) a mutation of T to C at nucleotide number 412,
 c) a mutation of A to G at nucleotide number 538,
 d) a mutation for substitution of A to T at nucleotide number 1012,
 e) a mutation by deletion of C at nucleotide number 1069,
 f) a mutation for substitution of C to G at nucleotide number 1094,
 g) a mutation of G to C at nucleotide number 1155,
 h) a mutation for substitution of T to C at nucleotide number 1220,
 i) a mutation of T to C at nucleotide number 1243,
 j) a mutation by deletion of C at nucleotide number 1271, and
 k) a mutation of T to G at nucleotide number 1336.

In a preferred embodiment the invention provides a mutant replication control region which:
 (i) conveys temperature sensitivity to a plasmid; and
 (ii) hybridizes to the mutant replication region nucleotide sequence of the invention under the following conditions: 1×SSC, 0.1% SDS, 65° C. and washed with 2×SSC, 0.1% SDS followed by 0.1×SSC, 0.1% SDS.

Similarly the invention provides a mutant replication control region which:
 (i) conveys temperature sensitivity to a plasmid; and
 (ii) is at least 90% identical to the mutant replication region nucleotide sequence of the invention.

Additionally the invention is concerned with a mutant replication gene having the nucleotide sequence as set forth in SEQ ID No:6.

The invention additionally relates to plasmids comprising the mutant replication regions and/or replication genes of the invention.

In a preferred embodiment the invention provides a method for the disruption of a bacterial chromosomal nucleotide sequence and selection for a single crossover event comprising:
 a) providing a host cell harboring a plasmid, said plasmid comprising:
  (i) a mutant replication control region of the invention;
  (ii) a selectable marker;
  (iii) an origin of replication facilitating replication in the host cell; and
  (iv) a nucleotide sequence of interest having homology to a chromosomal nucleotide sequence in said host cell genome;
 b) culturing the host cell of (a) at a permissive temperature wherein homologous recombination takes place between the sequence of interest and the chromosomal sequence such that a single crossover causes the plasmid to be integrated into the host genome at the point of the chromosomal sequence;
 c) culturing the host cell of (b) at a restrictive temperature wherein autonomous replication of the plasmid is inhibited; and
 d) selecting those host cells of (c) having a single crossover event on the basis of the selectable marker.

Similarly the invention provides a method for the disruption of a bacterial chromosomal nucleotide sequence and selection for a double crossover event comprising:
 a) providing a host cell harboring a plasmid, said plasmid comprising:
  (i) a mutant replication control of the invention;
  (ii) an origin of replication facilitating replication in the host cell; and
  (iii) anucleotide sequence of interest having homology to a chromosomal sequence in said host cell genome, said sequence of interest having a gene encoding a selectable marker inserted therein;
 b) culturing the host cell of (a) at a permissive temperature wherein homologous recombination takes place between the sequence of interest and the chromosomal sequence such that at least one crossover occurs on each side of the selectable marker thereby causing the selectable marker to be integrated into the host genome at the point of the chromosomal sequence;
 c) culturing the host cell of (b) at a restrictive temperature wherein autonomous replication of the plasmid is inhibited; and
 d) selecting those host cells of (c) having a double crossover event on the basis of the selectable marker.

Alternatively the invention provides a method for the chromosomal insertion of a nucleotide sequence and selection for a single crossover event comprising:
 a) providing a host cell harboring a plasmid, said plasmid comprising:
  (i) a mutant replication control region of the invention;
  (ii) a selectable marker;
  (iii) an origin of replication facilitating replication in the host cell;
  (iv) a first nucleotide sequence of interest having homology to a second chromosomal nucleotide sequence in said host cell genome; and
  (v) a sequence of interest;
 b) culturing the host cell of (a) at a permissive temperature wherein homologous recombination takes place between the first sequence of interest and the chromosomal sequence such that a single crossover causes the plasmid to be integrated into the host genome at the point of the chromosomal sequence;
 c) culturing the host cell of (b) at a restrictive temperature wherein autonomous replication of the plasmid is inhibited; and
 d) selecting those host cells of (c) having a single crossover event on the basis of the selectable marker.

In a similar embodiment the invention provides a method for the chromosomal insertion of a nucleotide sequence and selection for a double crossover event comprising:

a) providing a host cell harboring a plasmid, said plasmid comprising:
   (i) a mutant replication control region of the invention:
   (ii) an origin of replication facilitating replication in the host cell; and
   (iii) a cassette comprising
      1) a sequence of interest;
      2) a selectable marker; and
      3) regions of homology to a chromosomal sequence in said host cell genome such that said regions of homology flank the sequence of interest and the selectable marker;
b) culturing the host cell of (a) at a permissive temperature wherein homologous recombination takes place between the flanking regions of homology and the chromosomal sequence such that at least one crossover occurs on each side of the selectable marker and the sequence of interest thereby causing the selectable marker and the sequence of interest to be integrated into the host genome at the point of the chromosomal sequence;
c) culturing the host cell of (b) at a restrictive temperature wherein autonomous replication of the plasmid is inhibited; and
d) selecting those host cells of (c) having a double crossover event on the basis of the selectable marker and which have the sequence of interest inserted into the chromosome.

The invention is additionally concerned with a gram negative host cell comprising a mutant replication control region of the invention.

BRIEF DESCRIPTION OF FIGURES AND SEQUENCE DESCRIPTIONS

Figure 1:
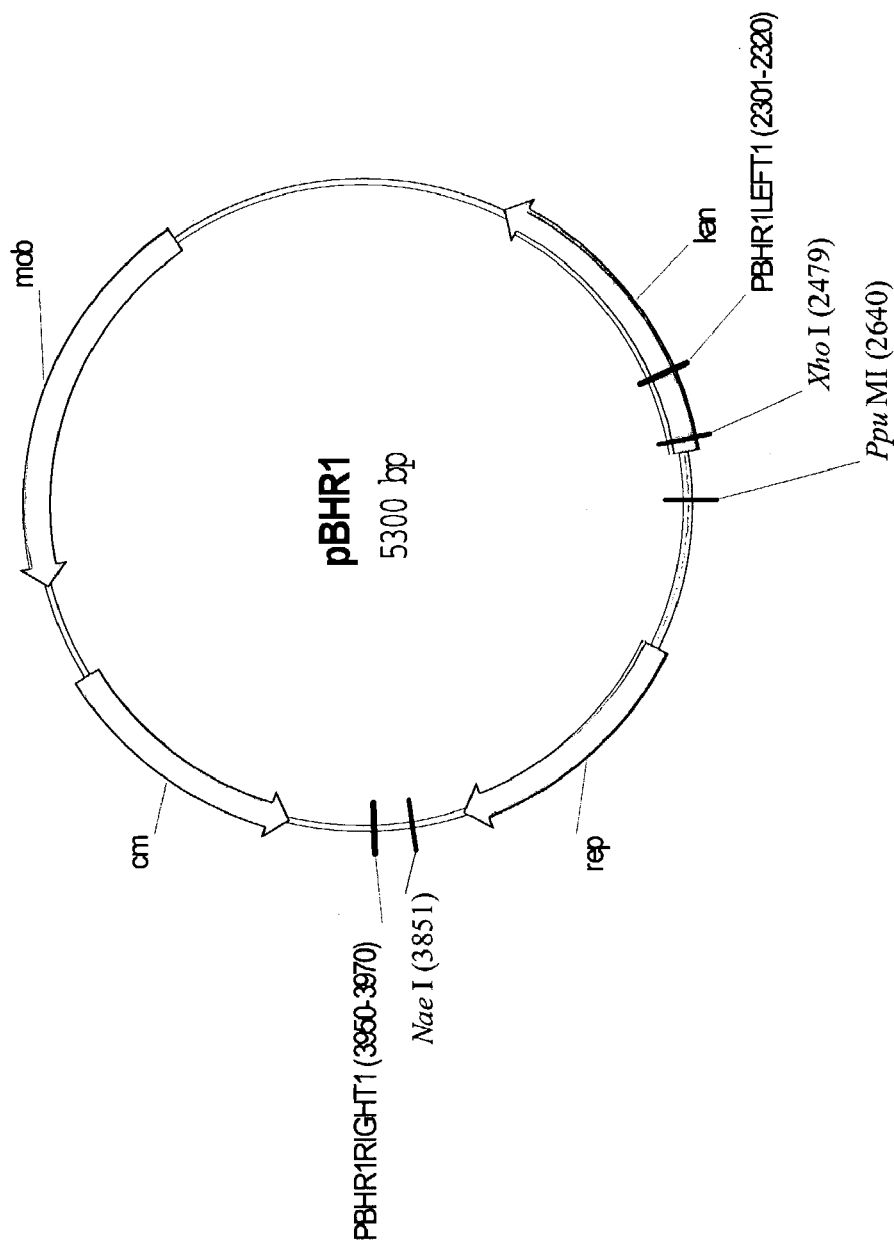
FIG. 1 is a map of plasmid pBHR1 showing the positions of ORFs, key restriction sites, and primer binding sites.

The following sequence descriptions and sequence listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the wild type replication control region of plasmid pBHR1, corresponding to the XhoI-NaeI fragment of the wild type plasmid (bases 2479–3851 of GenBank Y14439).

SEQ ID NOs:2–5 are the mutant replication control regions contained within temperature sensitive mutant plasmids pBHR1-3, pBHR1-4, pBHR1-5, and pBHR1-6, respectively.

SEQ ID NO:6 is the nucleotide sequence of the mutant rep gene of the invention.

SEQ ID NOs:7 and 8 are the primers PBHR1LEFT1 and PBHR1RIGHT1, respectively, that were used to amplify the replication control region in pBHR1.

SEQ ID NOs:9–12 encode primers PBHR1LEFT2, PBHR1LEFT3, PBHR1RIGHT2, and PBHR1RIGHT3, respectively, used for sequencing the replication control region of temperature sensitive mutant plasmids.

DETAILED DESCRIPTION OF THE INVENTION

The present invention provides a mutant replication control region conveying temperature sensitivity to plasmids on which it resides and plasmids comprising the same. Plasmids of the present invention are able to autonomously replicate at permissive temperatures; however they are inhibited from replicating at restrictive temperatures. The suite of mutant plasmids so created will be particularly useful for studies that require plasmid curing, plasmid chasing, and for the creation of single and double crossover mutants via homologous recombination.

Definitions

In this disclosure, a number of terms and abbreviations are used. The following definitions are provided.

"Open reading frame" is abbreviated ORF.

"Polymerase chain reaction" is abbreviated PCR.

"Temperature sensitive" is abbreviated Ts.

The term "replication control region" means a region of DNA containing a rep gene, or a gene having homology to a rep gene, that is responsible for controlling the replication of a plasmid. Typically replication control regions of the invention are isolated from pBHR1 GenBank Accession No. Y14439, and commercially available through MoBiTec (Göttingen, Germany). Generally, replication control regions of interest in the present invention will comprise the rep gene and up to about 1 kB of flanking DNA on either side of the gene. For example, with respect to wild type pBHR1, as defined by Genbank Accession Number Y14439, the replication control region will herein be defined as that portion contained between nucleotides 2479–3851; the rep gene itself is located between nucleotides 3037–3711.

The term "mutant replication control region" or "mutant plasmid replication control region" or "temperature sensitive replication control region" refers to the replication control region comprising about 1400 bp, isolated from the pBHR1 plasmid (GenBank Accession No. Y14439) wherein mutations have been inserted in the sequence such that the region conveys temperature sensitivity to a plasmid on which it resides.

The term "temperature sensitive" is abbreviated "Ts" and refers to the behavior of a plasmid in a host cell such that the plasmid is autonomously replicable at permissive temperatures but makes autonomous replication of the plasmid impossible at a temperature higher than that permissive temperature (i.e., the restrictive temperature).

In the present invention, the term "permissive temperature" refers to a temperature that permits autonomous replication of the Ts-plasmid. In contrast, the term "restrictive temperature", or "non-permissive temperature" refers to a temperature that makes autonomous replication of the plasmid impossible. This restrictive temperature must, however, be compatible with the viability of the host strain and enable growth of the microbial host. Many bacteria can grow at 20° C. to 42° C. The border of the permissive temperature and the restrictive temperature is within the range of, for example, 37° C. to 41° C., more specifically about 40° C. The permissive temperature is preferably about 30° C. to about 36° C., while the restrictive temperature is preferably from about 36° C. to about 45° C.

The term "gene disruption" will be used interchangeably with "gene knock out" and refers to the process of interfering with the coding region of a gene such that no functional gene product is expressed.

The terms "single crossover event" and "plasmid integration" are used interchangeably and mean the incorporation of a plasmid or vector into the genome of a host cell via homologous recombination between regions of homology between a DNA region within a chromosomal integration vector and a region within the host's chromosomal DNA.

The term "double crossover event" means the homologous recombination between a DNA region within a chromosomal integration vector and a region within the host's chromosomal DNA that results in the replacement of the chromosomal region with the homologous region of the chromosomal integration vector.

The term "chromosomal integration" means that a chromosomal integration vector becomes congruent with the chromosome of a microorganism through recombination between homologous DNA regions on the chromosomal integration vector and within the chromosome.

The term "pBHR1" will refer to the broad host range plasmid pBHR1, as described in GenBank Accession No. Y14439, and commercially available through MoBiTec (Göttingen, Germany). A "pBHR1 plasmid" will refer to any plasmid having the replication control region of the pBHR1 plasmid, or any replication control region having significant homology thereto.

The term "mutant pBHR1" or "Ts-pBHR1" will refer to any modified pBHR1 plasmid possessing a temperature sensitive replication control region. Preferred temperature sensitive mutant plasmids of the present invention are pBHR1-3, pBHR1-4, pBHR1-5, and pBHR1-6.

The term "rep" refers to a replication gene of a plasmid responsible for the replication characteristics of the plasmid.

The term "mutagenic procedure" refers to a process of subjecting a plasmid, or host cell comprising a plasmid, to various mutagizing agents such that mutations occur within a specific region of DNA and said mutations can be recognized through screening procedures or selection procedures. Of particular interest in the present invention are mutations occurring in the replication control regions of plasmids.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with an appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Gene" refers to a nucleic acid fragment that expresses a specific protein, or RNA including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. The term "expressible gene" or "expressible sequence" will refer to a gene or DNA fragment that is intact and able to encode a protein or perform its natural function. An "expressible gene" is to be contrasted with a "disrupted gene" or "inactivated gene" which is not able to encode a protein or perform its natural function due to disruption or mutation of the gene sequence.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence or RNA sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Transformation" refers to the transfer of a nucleic acid fragment into the genome of a host organism, resulting in genetically stable inheritance. There are a variety of methods well known to those in the art for microbial transformation including, but not limited to: electroporation, heat shock, conjugation, biolistic bombardment, etc. Host organisms containing the transformed nucleic acid fragments are referred to as "transgenic" or "recombinant" or "transformed" organisms.

The term "expression", as used herein, refers to the transcription and stable accumulation of sense (mRNA) or antisense RNA derived from the nucleic acid fragment of the invention. Expression may also refer to translation of mRNA into a polypeptide.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T.

Molecular Cloning: A Laboratory Manual, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook, J. et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "portion" of an amino acid or nucleotide sequence is that comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993); see also www.ncbi.nim.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "portion" of a nucleotide sequence comprises enough of the sequence to specifically identify and/or isolate a nucleic acid fragment comprising the sequence. The instant specification teaches partial or complete amino acid and nucleotide sequences encoding a temperature sensitive replication control region of pBHR1. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including—but not limited to—those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humana: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the ALIGNX program of the Vector NTI bioinformatics computing suite (InforMax Inc., Bethesda, Md.). Multiple alignment of the sequences was performed using the Clustal method of alignment (Higgins and Sharp CABIOS. 5:151-153 (1989)) with default parameters (GAP OPENING PENALTY=10, GAP EXTENSION PENALTY=0.05, GAP SEPARATION PENALTY RANGE=8). Default parameters for pairwise alignments using the Clustal method were: KTUPLE 1, GAP PENALTY=3, WINDOW=5 and DIAGONALS SAVED=5. Suitable nucleic acid fragments (isolated polynucleotides of the present invention) are at least about 70% identical, preferably at least about 80% and most preferably about 90% identical to the nucleotides defining the replication control regions of the invention. Suitable nucleic acid fragments not only have the above homologies but also the characteristics of temperature sensitivity.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the replication control region as set forth in SEQ ID NOs:2-5.

The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "sequence analysis software" refers to any computer algorithm or software program that is useful for the analysis of nucleotide or amino acid sequences. "Sequence analysis software" may be commercially available or independently developed. Typical sequence analysis software will include, but are not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403-410 (1990)); 3.) the Vector NTI bioinformatics computing suite (InforMax Inc., Bethesda, Md.); and 4.) the FASTA program incorporating the Smith-Waterman algorithm (W. R. Pearson, *Comput. Methods Genome Res.*, [Proc. Int. Symp.] (1994), Meeting Date 1992, 111-20. Ed.: Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used herein are well known in the art as described by Sambrook, J., Fritsch, E. F. and Maniatis, T., Molecular Cloning: A Laboratory Manual, 2$^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987).

Elements of the Plasmid

The present invention provides a replication control region comprising about 1400 bp of pBHR1 which has been mutated to convey temperature sensitivity to a plasmid on which it resides.

The replication control region of the invention was isolated after mutagenesis of the pBHR1 plasmid and introduction of the mutagenized plasmid into a suitable host cell for screening.

Methods of DNA mutagenesis are common and well known in the art. For example, DNA may be exposed to a variety of agents such as radiation or chemical mutagens and then transformed into an appropriate host and screened for the desired phenotype. When creating mutations through radiation either ultraviolet (UV) or ionizing radiation may be used. Suitable short wave UV wavelengths for genetic mutations will fall within the range of 200 nm to 300 nm where 254 nm is preferred. UV radiation in this wavelength principally causes changes within nucleic acid sequence from guanidine and cytosine to adenine and thymidine. Long wave UV mutations using light in the 300 nm to 400 nm range are also possible but are generally not as effective as the short wave UV light unless used in conjunction with various activators (e.g., psoralen dyes) that interact with the DNA.

Mutagenesis with chemical agents is also effective for generating mutants. Commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, 2$^{nd}$ ed. (1989) Sinauer Associates: Sunderland, Mass., or Deshpande, Mukund V., *Appl. Biochem. Biotechnol.*, 36: 227 (1992), herein incorporated by reference.

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See Brock, supra.; and DeMancilha et al., *Food Chem.*, 14:313 (1984).

Plasmids of the present invention were mutagenized and introduced into host cells and screened for plasmids which replicate at permissive temperatures of about 30° C. to 36° C. but not at restrictive temperatures of about 37° C. to 45° C. The desired plasmids were then re-isolated and the replication control region was sequenced. When the mutant plasmid replication control region (SEQ ID NOs:2–5) was compared with the wildtype pBRH1 replication control region (SEQ ID No:1) the following mutations were observed:

(a) a mutation of T to A at nucleotide number 72,
(b) a mutation of T to C at nucleotide number 412,
(c) a mutation of A to G at nucleotide number 538,
(d) a mutation for substitution of A to T at nucleotide number 1012,
(e) a mutation by deletion of C at nucleotide number 1069,
(f) a mutation for substitution of C to G at nucleotide number 1094,
(g) a mutation of G to C at nucleotide number 1155,
(h) a mutation for substitution of T to C at nucleotide number 1220,
(i) a mutation of T to C at nucleotide number 1243,
(j) a mutation by deletion of C at nucleotide number 1271, and
(k) a mutation of T to G at nucleotide number 1336.

These mutations had the effect of conveying temperature sensitivity to the plasmid on which the mutant replication control region resided.

A representative mutant replication gene (SEQ ID No:6) which will convey temperature sensitivity to the plasmid on which the mutant replication gene resides, may optionally contain at least one point mutation independently selected from the group consisting of:

(a) a mutation for substitution of A to T at nucleotide number 454 (corresponding to position 1012 of the replication control region),
(b) a mutation for substitution of C to G at nucleotide number 536 (corresponding to position 1094 of the replication control region),
(c) a mutation of G to C at nucleotide number 597 (corresponding to position 1155 of the replication control region), and
(d) a mutation for substitution of T to C at nucleotide number 662 (corresponding to position 1220 of the replication control region).

It is thus an aspect of the invention to provide a method for the generation and isolation of a temperature sensitive mutant plasmid replication control region comprising:

a) providing a pBHR1 plasmid;
b) subjecting the plasmid of (a) to a mutagenic procedure wherein mutations are introduced into the replication control region of the pBHR1 plasmid;
c) culturing the mutagenized plasmid of (b) at a permissive temperature;
d) selecting at least one plasmid of (c) which does not replicate at a restrictive temperature; and
e) isolating mutant replication control regions from the plasmids of (d).

It is contemplated that other sequences having the same or other mutations in this particular replication control region will give rise to temperature sensitivity. It will be expected for example that sequences having a high degree of homology to the present sequences and having the appropriate mutations will also convey temperature sensitivity. Thus it is an aspect of the invention to provide a mutant replication control region which: 1.) conveys temperature sensitivity to a plasmid; and 2.) hybridizes to the mutant nucleotide sequence of the invention under the following conditions: 1×SSC, 0.1% SDS, 65° C. and washed with 2×SSC, 0.1% SDS followed by 0.1×SSC, 0.1% SDS. Similarly it is an aspect of the invention to provide a mutant replication control region which conveys temperature sensitivity to a plasmid and is at least 90% identical to the nucleotide sequence of the mutant replication region of the invention.

Plasmids of the invention will additionally contain other elements well known and useful for replication and selection. For example, in addition to a replication control region conveying temperature sensitivity, plasmids will have an origin of replication that governs replication (ORI) of the plasmid in a particular host. The origin of replication is typically host specific and governs the host range of the plasmid. It is expected that the plasmid of the present invention will function in all gram negative bacteria and will be particularly useful in the genera *Acetobacter, Acinetobacter, Aeromonas, Agrobacterium, Alcaligenes, Anabaena, Azorizobium, Bartonella, Bordetella, Brucella, Burkholderia, Campylobacter, Caulobacter, Chromatium, Comamonas, Cytophaga, Deinococcus, Erwinia, Erythrobacter, Escherichia, Flavobacterium, Hyphomicrobium, Klebsiella, Methanobacterium, Methylbacterium, Methylobacillus, Methylobacter, Methylobacterium, Methylococcus, Methylocystis, Methylomicrobium, Methylomonas, Methylophilus, Methylosinus, Myxococcus, Pantoea, Paracoccus, Pseudomonas, Rhizobium, Rhodobacter, Salmonella, Shigella, Sphingomonas* and *Vibrio*.

For the plasmid to be a useful tool, it generally will contain a selectable marker. Selectable markers are common and well known in the art and typically are those genes that convey antibiotic resistance to the host cell. Suitable selectable markers for use in the present invention include, but are not limited to: genes encoding ampicillin (Amp) resistance, kanamycin (Kan) resistance, tetracycline resistance, chloramphenicol resistance, and spectinomycin resistance. Also suitable as genetic markers are those genes encoding metal resistance, substrate-utilization, and genes encoding fluorescent and bioluminescent proteins (e.g. green fluorescent proteins, Lux genes), as well as lacZ, gfp, cat, galK, inaZ, luc, luxAB, bgaB, nptII, phoA, uidA and xylE. Other suitable bacterial and yeast markers may be found in Sambrook, J. et al., supra.

One fortuitous aspect of the plasmids of the invention is that the replication control region differs from conventionally known plasmids (e.g., plasmids belonging to the incompatibility groups C, N, P, Q and W), and it is not incompatible with these plasmids. Thus these plasmids can be used in microbes together with more common plasmids belonging to the incompatibility groups C, N, P, Q and W.

Typically, plasmids are used for the expression of foreign DNA in a host cell. In addition to the elements recited above the plasmids of the invention will contain other elements that will facilitate the insertion or expression of foreign DNA which is to be carried on the plasmid. For example, it will be useful for the plasmid to have a region 5' of the foreign DNA which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific host cell species. Where it is desired to express or over-express a foreign gene, initiation control regions, or promoters will be useful to drive gene expression. Virtually any promoter should be capable of driving the gene; non-limiting examples include lac, ara, tet, trp, $IP_L$, $IP_R$, T7, tac, and trc.

Plasmid—Methods of Use

The temperature sensitive plasmids (Ts-plasmids) of the present invention can be utilized for a variety of purposes, including: 1.) plasmid curing (whereby it is desirable to eliminate a plasmid from a bacterial strain); 2.) plasmid chasing (whereby it is possible to remove, or "chase", other plasmids from a bacterial strain that are incompatible with the subsequently introduced plasmid); and 3.) for the creation of single and double crossover mutants via homologous recombination (whereby a particular region of DNA can be integrated into a host chromosome from a plasmid).

Plasmid curing is a process whereby free form plasmids (i.e., those not integrated into the chromosome of the bacteria) can be experimentally removed from a cell. In general, this process involves growing cells for many generations without a selective agent (e.g., antibiotic), such that the plasmid is "diluted" from the cell culture. This occurs due to the lack of selective pressure, whereby cells are constantly "losing" the plasmid by cell division. By use of the temperature sensitive plasmids, it is possible to dramatically expedite this process of curing, by increasing the temperature of the cell culture to the restrictive temperature. Since plasmids are not able to replicate at the restrictive temperature, the cells gradually lose the plasmid by cell division and cell dilution.

An additional embodiment of the present invention permits plasmid "chasing". This process allows removal of all plasmids within a particular microbe that are incompatible with the present plasmids. This strategy requires that the "chased" plasmid and the Ts-plasmid possess different antibiotic resistances for purposes of selection. The process for plasmid chasing involves introduction of a Ts-plasmid into the bacterial host. Those plasmids that are incompatible with the Ts-plasmid are unable to co-exist and are deleted from the host cell. Facile selection for those plasmids carrying the Ts replication control region is then possible by antibiotic selection. As a subsequent step in the plasmid "chasing" process, one could readily cure the bacterial host of Ts-plasmid, if it was desirable to obtain a plasmid-free host. It is well known to those skilled in the art that a strategy of plasmid "chasing" would have tremendous utility in certain specialized situations when it is desirable to recover a host strain without a plasmid.

The plasmid of the present invention can additionally be utilized for incorporation of a DNA fragment into a chromosome, gene substitution, or gene disruption using homologous recombination. For example, incorporation of a DNA fragment into a chromosome can be performed as follows. First, a DNA fragment which has a DNA sequence homologous to a DNA sequence present on a chromosome of a bacterium is ligated into the Ts-plasmid of the present invention to construct a recombinant plasmid, and the bacterium is transformed with the recombinant plasmid. A transformant is then cultured at permissive temperatures, such that homologous recombination occurs between the DNA fragment on the Ts-plasmid and the homologous DNA sequence present on the chromosome of the bacterium. Thus, the DNA fragment on the plasmid is incorporated into the chromosome. If the plasmid is also incorporated into the chromosome, this is known as a single crossover event. The DNA sequence on the chromosome is disrupted by the incorporation of the DNA fragment on the plasmid and the plasmid itself. The DNA fragment cloned into the plasmid can correspond to a precise gene, which may be specifically inactivated by integration of the plasmid in the chromosomal copy of the gene.

Thus, according to one of its aspects, the subject of the present invention is a method for the inactivation of a gene present in the chromosome of a microbe, by producing single crossover mutants, characterized by the following steps:

a) providing a host cell harboring a plasmid, said plasmid comprising:
   (i) a mutant replication control region of the invention;
   (ii) a selectable marker;
   (iii) an origin of replication facilitating replication in the host cell; and
   (iv) an expressible nucleotide sequence of interest having homology to a chromosomal nucleotide sequence in said host cell genome;

b) culturing the host cell of (a) at a permissive temperature wherein homologous recombination takes place between the sequence of interest and the chromosomal sequence such that a single crossover causes the plasmid to be integrated into the host genome at the point of the chromosomal sequence;

c) culturing the host cell of (b) at a restrictive temperature wherein autonomous replication of the plasmid is inhibited; and d) selecting those host cells of (c) having a single crossover event on the basis of the selectable marker.

In some cases, it is desirable to remove all or part of the genetic material introduced into the bacterial chromosome by the methods according to the present invention. To accomplish this objective, at the end of step (d), the surviving cells are cultured again at a permissive temperature on non-selective medium.

In contrast, a double crossover event permits complete replacement of the DNA chromosomal sequence with the DNA fragment present on the Ts-plasmid. This may also enable inactivation of a specific gene in the chromosome. When a microbe obtained as described above is cultured to cause homologous recombination in the form of a double crossover event, the DNA fragment originally present on the Ts-plasmid is stably incorporated into the chromosome, while the DNA sequence originally present on the chromosome is excised from the chromosome and incorporated into the Ts-plasmid in its free form. The excised DNA sequence within the Ts plasmid can be completely removed from the cell, when the microbe is cultured at restrictive temperatures. In this way, the DNA sequence on the chromosome can be replaced with the introduced DNA fragment. This strategy permits genetic modification of microbes that are supposedly difficult to transform because the Ts-plasmids can be moved into cells by conjugation.

Thus, according to one of its aspects, the subject of the present invention is a method for the inactivation of a gene present in the chromosome of a microbe, by producing double crossover mutants, characterized by the following steps:

a) providing a host cell harboring a plasmid, said plasmid comprising:
   (i) a mutant replication control region of the invention;
   (ii) an origin of replication facilitating replication in the host cell; and
   (iii) a nucleotide sequence of interest having homology to a chromosomal sequence in said host cell genome, said sequence of interest having a gene encoding a selectable marker inserted therein;

b) culturing the host cell of (a) at a permissive temperature wherein homologous recombination takes place between the sequence of interest and the chromosomal sequence such that at least one crossover occurs on each side of the selectable marker thereby causing the selectable marker to be integrated into the host genome at the point of the chromosomal sequence;

c) culturing the host cell of (b) at a restrictive temperature wherein autonomous replication of the plasmid is inhibited; and d) selecting those host cells of (c) having a double crossover event on the basis of the selectable marker.

After introduction of the vector plasmid into the microbe by transformation or by conjugation in step (a), the plasmid is allowed to establish itself in the microbial population, by replication at approximately 30–37° C. The selectable character is expressed in all the microbial organisms. When the temperature rises to approximately 42° C. (the restrictive temperature) in step (d), the plasmid in free form becomes incapable of replicating and is hence lost during subsequent cell divisions. Only the microbes in which this plasmid or part of this plasmid has become integrated in the chromosome by homologous recombination retain and transmit the genetic information carried by the plasmid, thereby enabling these microbial organisms to grow on the selective medium. The low-frequency integration events are thus selected in step (c) for single or double crossover events by recovering the microbes which multiply at 42° C. This method of gene inactivation can be repeated, since the Ts-plasmid can readily be cured from the transformed microbes, thereby allowing use of the Ts-plasmid again in a subsequent cycle of genetic transformation using the same antibiotic selection method.

In another embodiment, the microbial DNA present in the plasmid may be chosen from a library of chromosomal fragments for cloning, and there will be integration at random. The integration site of the plasmid differs from one microbe to another, and mutagenesis is thus produced.

The methods of the present invention may also be applied to a temperature-sensitive replicon carrying a transposon. Different transposons are available for mutagenizing the chromosome; however, in many cases, the Ts plasmid is employed as a carrier of one of these transposons. Each transposon carries a marker gene (e.g., a resistance gene). By applying the protocol described above (steps a to c, for the inactivation of a chromosomal gene by producing double crossover mutants), cells which have integrated the transposon in their chromosomes are obtained. These cells are selected by means of the transposon marker. In the case of transposition, the plasmid is not integrated in the chromosome.

According to another of its aspects, the invention provides a method enabling a heterologous (foreign) gene to be introduced into the chromosome of a microbe. The heterologous gene is incorporated into the chromosome of a microbe by a double crossover recombination event. For its implementation, a gene coding for a trait and any necessary elements required for its expression must be inserted into a fragment of DNA in the Ts-plasmid that is homologous to a DNA sequence in the chromosome of the microbe.

Protein Engineering

It is contemplated that many Ts mutant plasmids could be created within the replication control regions of pBHR1, in addition to pBHR1-3, pBHR1-4, pBHR1-5, and pBHR1-6 recited in the present examples. More specifically, a temperature sensitive replication control region derived from pBHR1 can be obtained by subjecting pBHR1 or a plasmid derived from pBHR1 to a mutagenesis treatment, and selecting a mutant plasmid that is autonomously replicable at a permissive temperature, but is not autonomously replicable at a restrictive temperature within the temperature range in which the preferred microbial hosts can grow. It is expected that any Ts-mutation would be localized within the replication control region.

Various methods are known for mutating a native gene sequence to produce a gene product with altered activity including, but not limited to: 1.) error prone PCR (Melnikov et al., *Nucleic Acids Research,* 27(4): 1056–1062 (Feb. 15, 1999)); 2.) site directed mutagenesis (Coombs et al., *Proteins* (1998), 259–311,1 plate. Ed.: Angeletti, Ruth Hogue. Academic: San Diego, Calif.); and 3.) "gene shuffling" (U.S. Pat. No. 5,605,793; U.S. Pat. No. 5,811,238; U.S. Pat. No. 5,830,721; and U.S. Pat. No. 5,837,458, incorporated herein by reference). Other well known mutagenesis treatments include in vitro treatment with hydroxylamine (see, for example, G. O. Humpherys et al., *Molec. Gen. Genet.,* 145:101–108 (1976)), treatments of microorganisms harboring a plasmid with UV irradiation, and mutagens used for usual mutagenesis treatments such as N-methyl-N'-nitro-N-nitrosoguanidine (NTG) and nitrous acid.

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double-stranded and can be of various lengths ranging from 50 bp to 10 kB. The sequences may be randomly digested into fragments ranging from about 10 bp to 1000 bp, using restriction endonucleases well known in the art (Sambrook, J. et al., supra). In addition to the instant microbial sequences, populations of fragments that are hybridizable to all or portions of the microbial sequence may be added. Similarly, a population of fragments that are not hybridizable to the instant sequence may also be added. Typically these additional fragment populations are added in about a 10 to 20 fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably the temperature is from about 80° C. to 100° C. The nucleic acid fragments may be reannealed by cooling. Preferably the temperature is from about 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, Taq polymerase, or any other DNA polymerase known in the art. The polymerase may be added to the random nucleic acid fragments prior to annealing, simultaneously with annealing, or after annealing. The cycle of denaturation, renaturation and incubation in the presence of polymerase is repeated for a desired number of times. Preferably the cycle is repeated from about 2 to 50 times, more preferably the sequence is repeated from 10 to 40 times. The resulting nucleic acid is a larger double-stranded polynucleotide ranging from about 50 bp to about 100 kB and may be screened for expression and altered activity by standard cloning and expression protocols (Sambrook, J. et al., supra).

Furthermore, a hybrid protein can be assembled by fusion of functional domains using the gene shuffling (exon shuffling) method (Nixon et al., PNAS, 94:1069–1073 (1997)). The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

DESCRIPTION OF THE PREFERRED EMBODIMENTS

As specific examples of the Ts-plasmid of the present invention, there can be mentioned the temperature sensitive plasmids obtained in the examples described below: pBHR1–3, pBHR1–4, pBHR1–5, and pBHR1–6. These plasmids encompass one or more of the following mutations in the wild type replication control region of pBHR1:

(a) a mutation of T to A at nucleotide number 72,
(b) a mutation of T to C at nucleotide number 412,
(c) a mutation of A to G at nucleotide number 538,
(d) a mutation for substitution of A to T at nucleotide number 1012,
(e) a mutation by deletion of C at nucleotide number 1069,
(f) a mutation for substitution of C to G at nucleotide number 1094,
(g) a mutation of G to C at nucleotide number 1155,
(h) a mutation for substitution of T to C at nucleotide number 1220,
(i) a mutation of T to C at nucleotide number 1243,
(j) a mutation by deletion of C at nucleotide number 1271, and
(k) a mutation of T to G at nucleotide number 1336.

In all cases, the nucleotide number is described according to the nucleotide numbering of SEQ ID No:1 (wild type); the rep gene is encoded between nucleotides 559–1233. This region encoded by SEQ ID No:1 corresponds with nucleotides 2479–3851 of the wild-type pBHR1 vector (GenBank Accession No. Y14439).

These Ts-pBHR1 plasmids are autonomously replicable at least at 30° C., but are not autonomously replicable at 42° C. in bacteria. It is well known to those skilled in the art that a variety of other Ts mutations could be generated within the replication control region of pBHR1 using the teachings of the present invention, in order to produce a Ts-pBHR1 mutant that has the same phenotype as that embodied by any of pBHR1–3, pBHR1–4, pBHR1–5, and pBHR1–6. Those plasmids so generated that contain a temperature sensitive replication control region and that allow autonomous replication of the plasmids at a permissive temperature but that do not allow the autonomous replication at a restrictive temperature within the temperature range in which the microbes can grow are also encompassed within the scope of the plasmids of the present invention.

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); by T. J. Silhavy, M. L. Bennan, and Enquist, L. W. Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-lnterscience (1987).

Restriction enzyme digestions, phosphorylations, ligations and transformations were done as described in Sambrook, J. et al., supra. Restriction enzymes were obtained from New England Biolabs (Boston, Mass.), GIBCO/BRL (Gaithersburg, Md.), or Promega (Madison, Wis.). Taq polymerase was obtained from Perkin Elmer (Branchburg, N.J.). Growth media was obtained from GIBCO/BRL (Gaithersburg, Md.).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s), and "kB" means kilobase(s).

Example 1

Isolation of Mutant Derivatives of Plasmid pBHR1 that are Temperature Sensitive for Replication This example describes how error prone PCR was used to induce mutations in plasmid pBHR1 that cause plasmid replication to be temperature sensitive. The rep gene was amplified by error prone PCR from pBHR1. The resulting PCR product was ligated to a restriction fragment derived from pBHR1 so that the original rep gene was replaced by the product of error prone PCR. Several mutant plasmids were identified that could be maintained in *E. coli* when grown at 30° C. but were lost from *E. coli* host cells grown at 42° C. in the absence of antibiotic selection. Sequence analysis indicated that each mutant plasmid had one or more mutations in or near the pBHR1 rep gene.

Error Prone PCR and Ligation of Product to pBHR1 Vector Backbone

Primers PBHR1LEFT1 (SEQ ID NO:7) and PBHR1RIGHT1 (SEQ ID NO:8) were used in a series of 100 µl error prone PCR reactions to amplify a 1,650 bp fragment from pBHR1 that contained the pBHR1 rep gene (FIG. 1). Each error prone PCR reaction was performed with AmpliTaq DNA polymerase (Applied Biosystems, Foster City, Calif.) in buffer supplied by the manufacturer (Gene-Amp® 10×PCR Buffer II) containing $MgCl_2$ (250 µM), dNTPs (200 µM of each), primers (PBHR1LEFT1 and PBHR1RIGHT1), and pBHR1 DNA (45 ng). In addition, each reaction contained from 0 to 250 µM $MnCl_2$. The reactions were incubated in a Perkin Elmer GeneAMP 9600 initially for 5 min at 94° C. and then for 25 cycles at 94° C. for 1 min, 60° C. for 1 min, and 72° C. for 1.5 min. After the last cycle, the samples were incubated at 72° C. for an additional 10 min. The amplified DNA was purified using a QIAquick PCR Purification Kit according to the manufacturer's instructions (QIAgen, Valencia, Calif.) and stored at −20° C. The purified PCR products from reactions that contained 0 µM, 75 µM or 200 µM $MnCl_2$ were each first cut with restriction endonuclease NaeI and then restriction endonuclease XhoI according to standard methods in buffers supplied by the manufacturer (Promega, Madison, Wis.). A 1,372 bp NaeI/XhoI restriction fragment was purified for each PCR product by electrophoresis of the NaeI/XhoI digested DNA in 0.8% low-melting-point agarose in TEA buffer, followed by excision of the appropriate bands. The NaeI/XhoI restriction fragments were extracted from the excised agarose by using a QIAquick Gel Extraction Kit according to the manufacturer's instructions (QIAgen).

The NaeI/XhoI digested PCR product was used to replace the wild-type rep gene of plasmid pBHR1 as follows. Plasmid pBHR1 was first cut with restriction endonuclease NaeI and then restriction endonuclease XhoI according to standard methods in buffers supplied by the manufacturer (Promega). A 4,328 bp NaeI/XhoI restriction fragment was purified by electrophoresis of the NaeI/XhoI digested pBHR1DNA in 0.8% low-melting-point agarose in TEA buffer followed by excision of the appropriate band. The NaeI/XhoI restriction fragment was extracted from the excised agarose by using a QIAquick Gel Extraction Kit according to the manufacturer's instructions (QIAgen). The background level of uncut or partially cut DNA in the gel-purified NaeI/XhoI restriction fragment was reduced by treating the NaeI/XhoI restriction fragment with restriction endonuclease PpuMI in buffer supplied by the manufacturer according to standard methods (Promega). The 4,328 bp NaeI/XhoI restriction fragment was again purified from the PpuMI digest by electrophoresis in low-melting-point agarose as described above.

The 4,328 bp NaeI/XhoI restriction fragment from pBHR1 was ligated to the 1,372 bp NaeI/XhoI restriction fragments derived from error prone PCR products by using T4 DNA ligase (Promega) according to standard methods at 16° C. for 16 h in buffer supplied by the manufacturer. The ligated DNA was removed from the reaction by using a QIAgen MinElute Reaction Cleanup Kit according to the manufacturer's instructions (QIAgen) and was suspended in water. The ligated DNA was electroporated into electrocompetent E. coli DH10B cells (Invitrogen Corporation, Carlsbad, Calif.) using a BioRad Gene Pulser II (BioRad Laboratories, Hercules, Calif.) according to standard methods (voltage 2.5 kV, capacitance 25 µF, and 200 ohms). The transformed cells were spread on LB agar containing 50 µg/mL kanamycin (LBkan agar) and incubated for 18 h at 30° C.

Identification of Temperature Sensitive Mutants

Transformants containing mutant plasmids that were temperature sensitive for replication were identified by replica plating transformants onto LB agar and LBkan agar. The LBkan agar replicas were incubated for 18 h at 30° C., and the LB agar replicas were incubated for 18 h at 42° C. The LB agar replicas were replica plated to LBkan agar and incubated for 18 h at 42° C. Four transformants that failed to grow on LBkan agar at 42° C. were presumed to have pBHR1 temperature sensitive replication mutants (pBHR1-3, pBHR1-4, pBHR1-5, pBHR1-6) and were selected for further characterization. In addition, two transformants with plasmids that did not display temperature sensitivity (pBHR1-1, pBHR1-2) were selected for use as controls during further characterization. Plasmid DNA was extracted from each of these 6 transformants. The plasmid DNA was electroporated into E. coli DH10B as before. Two transformants (i.e., a pair of transformants with the same plasmid) were selected from each transformation for further characterization. The transformants are listed in Table 1.

TABLE 1

Characteristics Of Transformants Selected For Further Analysis

| Transformant | Temperature sensitive[1] | $MnCl_2$ concentration[2] |
|---|---|---|
| DH10B(pBHR1-1)A | − | 0 |
| DH10B(pBHR1-1)K | − | 0 |
| DH10B(pBHR1-2)B | − | 0 |
| DH10B(pBHR1-2)L | − | 0 |
| DH10B(pBHR1-3)C | + | 75 µM |
| DH10B(pBHR1-3)D | + | 75 µM |
| DH10B(pBHR1-4)E | + | 200 µM |
| DH10B(pBHR1-4)F | + | 200 µM |
| DH10B(pBHR1-5)G | + | 200 µM |
| DH10B(pBHR1-5)H | + | 200 µM |
| DH10B(pBHR1-6)I | + | 200 µM |
| DH10B(pBHR1-6)J | + | 200 µM |

[1]Indicated by failure to grow on LBkan agar at 42° C. after growth on LB agar at 42° C.
[2]Refers to the $MnCl_2$ concentration used during error prone PCR. Error prone PCR occurred in the presence of $MnCl_2$.

Confirmation of the Temperature Sensitive Replication Phenotype

The temperature sensitive replication phenotype of plasmids pBHR1-3, pBHR1-4, pBHR1-5 and pBHR1-6 was confirmed in the following experiment. DH10B(pBHR1-1) A, DH10B(pBHR1-2)B, DH10B(pBHR1-3)C, DH10B (pBHR1-4)E, DH10B(pBHR1-5)G and DH10B (pBHR1-6)I were inoculated into 10 mL of LB medium with 50 µg/mL of kanamycin in separate 125 mL Erlenmyer flasks. The flasks were incubated in a shaking water bath at 30° C. for 20 h. Each culture was diluted 1:10,000 into fresh LB medium to form 3 new 10 mL cultures. The first set of cultures was incubated in a shaking water bath at 30° C. without kanamycin. The second set of cultures was supplemented with 50 µg/mL of kanamycin and incubated in a shaking water bath at 30° C. The third set of cultures was incubated in a shaking water bath at 42° C. without kanamycin. After 22 h of incubation, all of the cultures were serially diluted in LB medium, and the serial dilutions were plated on LB agar and LBkan agar for viable counts. The viable count plates were incubated for 18 h at 30° C.

The data in Table 2 indicated that the numbers of kanamycin resistant bacteria did not significantly differ between cultures grown either with or without kanamycin at 30° C. The number of kanamycin resistant colonies was about 10% of the total number of colonies for strains DH10B (pBHR1-1)A and DH10B(pBHR1-2)B that were grown at 42° C. without kanamycin. This observation indicated that plasmids with an unaltered rep gene (pBHR1-1 and pBHR1–2) were slightly unstable during growth at 42° C. However, the number of kanamycin resistant colonies was less than 0.04% of the total number of colonies for strains containing plasmids with mutant rep genes (i.e., DH10B (pBHR1–3)C, DH10B(pBHR1–4) E, DH10B(pBHR1–5)G, DH10B(pBHR1–6)I). This observation indicated that pBHR1–3, pBHR1–4, pBHR1–5 and pBHR1–6 were readily lost from host cells during growth at 42° C.

TABLE 2

Loss of Mutant Plasmids from E. coil Grown at 42° C.

| Strain | Culture Condition | Viable Count (x $10^9$ CFU[1]) | |
|---|---|---|---|
| | | LB agar | LBkan agar |
| DH10B(pBHR1-1)A | 30° C. | 4.8 | 5.4 |
| DH10B(pBHR1-2)B | | 5.4 | 5.1 |
| DH10B(pBHR1-3)C | | 4.4 | 1.3 |
| DH10B(pBHR1-4)E | | 4.1 | 2.9 |
| DH10B(pBHR1-5)G | | 4.9 | 4.4 |
| DH10B(pBHR1-6)I | | 5.1 | 2.0 |
| DH10B(pBHR1-1)A | 30° C. with kanamycin | 3.7 | 6.8 |
| DH10B(pBHR1-2)B | | 3.6 | 6.5 |
| DH10B(pBHR1-3)C | | 3.1 | 4.5 |
| DH10B(pBHR1-4)E | | 3.7 | 5.4 |
| DH10B(pBHR1-5)G | | 3.7 | 5.5 |
| DH10B(pBHR1-6)I | | 4.3 | 5.6 |
| DH10B(pBHR1-1)A | 42° C. | 2.8 | 0.18 |
| DH10B(pBHR1-2)B | | 2.1 | 0.15 |
| DH10B(pBHR1-3)C | | 1.2 | 0.00048 |
| DH10B(pBHR1-4)E | | 2.0 | 0.00042 |
| DH10B(pBHR1-5)G | | 2.0 | 0.00046 |
| DH10B(pBHR1-6)I | | 2.0 | 0.00052 |

Example 2

Sequence of the Ts Replication Control Region in Mutant Derivatives of Plasmid pBHR1

This example describes the sequence of the region that was subjected to error prone PCR for each temperature sensitive replication mutant derived from pBHR1, as described in Example 1. Plasmids pBHR1–5 and pBHR1–6 each had a single different base pair change. Plasmids pBHR1–3 and pBHR1–4 each had multiple base pair changes.

Figure 2:
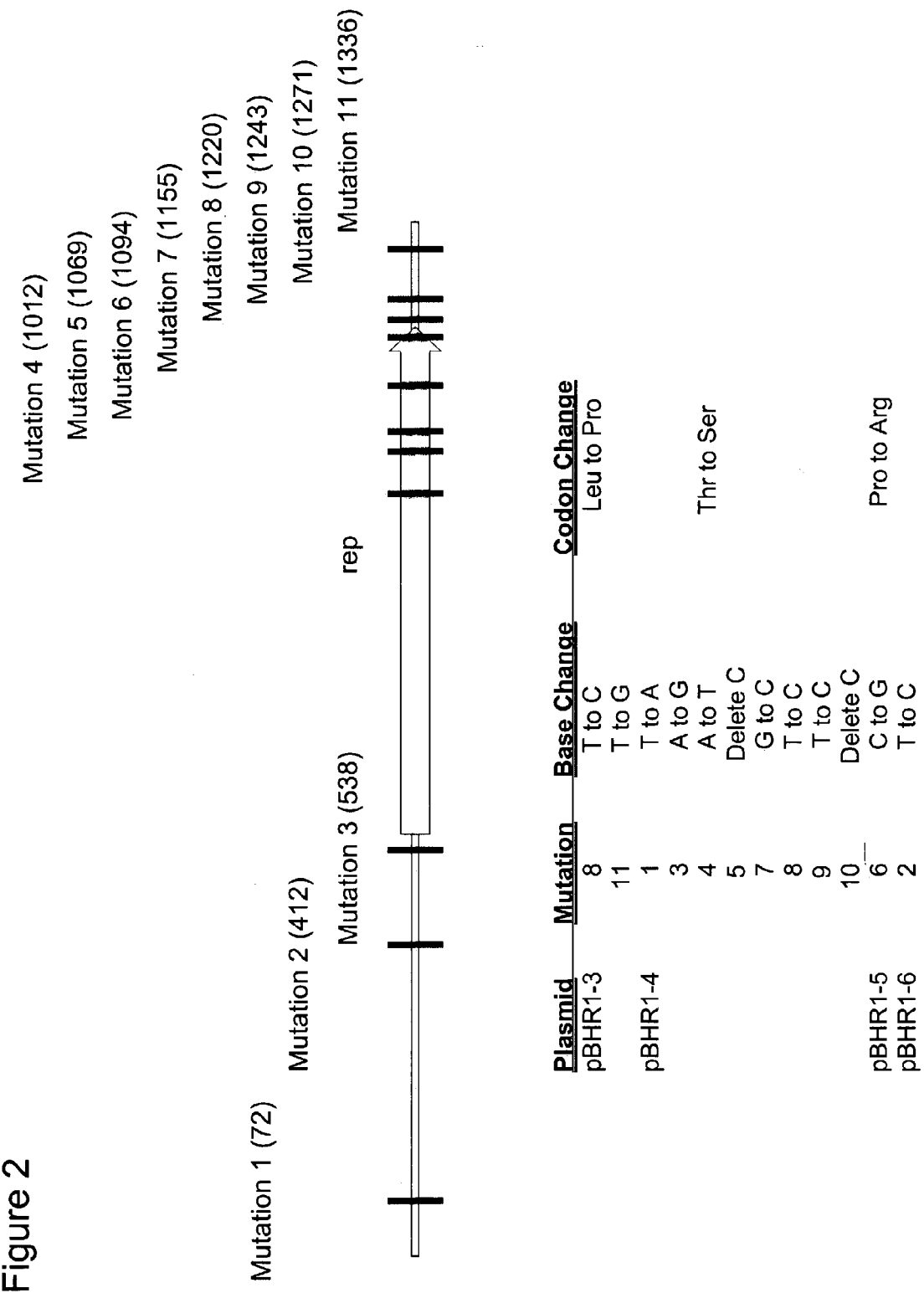
FIG. 2 is a map of the region of pBHR1 that was subjected to error prone PCR and a summary of all mutations created.

Primers PBHR1LEFT1 (SEQ ID NO:7) and PBHR1RIGHT1 (SEQ gID No:8) were used to amplify a 1,650 bp fragment from each of the pBHR1 derivatives listed in Table 1 that contained the pBHR1 rep gene (FIG. 1). The PCR products were sequenced on an automated ABI sequencer (Applied Biosystems, Foster City, Calif.). The sequencing reactions were initiated with PBHR1LEFT1, PBHR1LEFT2 (SEQ ID No:9), PBHR1LEFT3 (SEQ ID No:10), PBHR1RIGHT1, PBHR1RIGHT2 (SEQ ID No:11) and PBHR1RIGHT3 (SEQ ID No:12). The resulting sequences were assembled using ContigExpress which is a component of VectorNTI Suite 6.0 (InforMax, Inc., Bethesda, Md.). The portion of each assembled sequence between the NaeI and XhoI restriction sites was aligned with the corresponding wild type pBHR1 sequence (SEQ ID No:1, derived from GenBank Accession No. Y14439 and corresponding to nucleotides 2479–3851 of the wild type plasmid) using AlignX which is also a component of VectorNTI Suite 6.0. The differences between the mutant plasmids and pBHR1 are summarized in FIG. 2. Mutations were numbered in sequence from left to right. The number in parentheses indicates the base pair position of each mutation.

Plasmid pBHR1–5 (SEQ ID No:4) has a single base pair change in the rep gene. Therefore, mutations that change Pro to Arg in codon 362 result in temperature sensitive replication of pBHR1.

Plasmid pBHR1–6 (SEQ ID No:5) also has a single base pair change. The T to C change at base pair position 412 is located within one of the repeated sequences that characterize the origin of replication of pBHR1 (Antoine and Locht, *Mol. Microbiol.* 6:1785–1799 (1992); Szpirer et al., *J. Bacteriol.* 183:2101–110 (2001)). The origin of replication is the binding site for the rep gene product. Therefore, Mutation 2 (and possibly other base pair changes in the repeated sequences) is likely to alter the interaction of the rep gene product and the origin of replication so that plasmid replication is defective at 42° C.

Plasmid pBHR1–3 (SEQ ID No:2) has two mutations. Mutation 8 is located within the rep gene and causes a change of Leu to Pro in codon 404. Mutation 11 is located outside of and on the 3' side of rep. Although it is possible that mutation 11 affects a regulatory sequence, it is most likely that Mutation 8 and other mutations in codon 404 that change Leu to Pro cause temperature sensitive replication of pBHR1.

Plasmid pBHR1–4 (SEQ ID No:3) has 8 mutations. Mutations 1 and 3 are on the 5' side of the rep gene. These mutations could affect the origin of replication and/or the promoter for transcription of rep. Mutation 4 is a change of A to G that results in a change of Thr to Ser in codon 335. Mutation 5 is a one base pair deletion in codon 353 that changes the reading frame for translation of all down stream codons. As result, the rep open reading frame is shortened by 21 codons, and Mutations 7, 8, 9 and 10 are outside of the shortened open reading frame. It is not known which specific mutation or combination of mutations causes temperature sensitive replication by pBHR1–4.

What is claimed is:

1. A mutant replication region which is at least 95% identical to the a nucleotide sequence as set forth in SEQ ID NO:1, and which has at least one point mutation independently selected from the group consisting of:
   a) a mutation of T to A at nucleotide number 72,
   b) a mutation of T to C at nucleotide number 412,
   c) a mutation of A to G at nucleotide number 538,
   d) a mutation of A to T at nucleotide number 1012,
   e) a mutation by deletion of C at nucleotide number 1069,
   f) a mutation of C to G at nucleotide number 1094,
   g) a mutation of G to C at nucleotide number 1155,
   h) a mutation of T to C at nucleotide number 1220,
   i) a mutation of T to C at nucleotide number 1243,
   j) a mutation by deletion of C at nucleotide number 1271, and
   k) a mutation of T to G at nucleotide number 1336,
wherein said mutant replication control region conveys temperature sensitivity to a plasmid.

2. A mutant replication control region according to claim 1 selected from the group consisting of SEQ ID NO:2, SEQ ID NO:3, SEQ ID NO:4, and SEQ ID NO:5.

3. A plasmid comprising the mutant replication control region of claim 1.

4. The plasmid of claim 3 wherein the plasmid replicates in gram negative bacteria.

5. The plasmid of claim 4 wherein the gram negative bacteria is selected from the group consisting of *Acetobacter, Acinetobacter, Aeromonas, Agrobacterium, Alcaligenes, Anabaena, Azorizobium, Bartonella, Bordetella, Brucella, Burkholderia, Campylobacter, Caulobacter, Chromatium, Comamonas, Cytophaga, Deinococcus, Erwinia, Erythrobacter, Escherichia, Flavobacterium, Hyphomicrobium, Klebsiella, Methanobacterium, Methanbacterium, Methylobacillus, Methylobacter, Methylobacterium, Methylococcus, Methylocystis, Methylomicrobium, Methylomonas, Methylophilus, Methylosinus, Myxococcus, Pantoea, Paracoccus, Pseudomonas, Rhizobium, Rhodobacter, Salmonella, Shigella, Sphingomonas* and *Vibrio*.

6. The plastnid of claim 4 wherein the plasmid is temperature sensitive and autonomously replicates at a permissive temperature and will not autonomously replicate at a restrictive temperature.

7. The plasmid of claim 6 wherein the permissive temperature is from about 30° C. to 36° C. and the restrictive temperature is from about 37° C. to 45° C.

8. A gram negative host cell comprising a mutant replication control region according to claim 1.

9. The host cell according to claim 8 selected from the group consisting of *Acetobacter, Acinetobacter, Aeromonas, Agrobacterium, Alcaligenes, Anabaena, Azorizobium, Bar-*

*tonella, Bordetella, Brucella, Burkholderia, Campylobacter, Caulobacter, Chromatium, Comamonas, Cytophaga, Deinococcus, Erwinia, Erythrobacter, Escherichia, Flavobacterium, Hyphomicrobium, Klebsiella, Methanobacterium, Methylbacterium, Methylobacillus, Methylobacter, Methylobacterium, Methylococcus, Methylocystis, Methylomicrobium, Methylomonas, Methylophilus, Methylosinus, Myxococcus, Pantoea, Paracoccus, Pseudomonas, Rhizobium, Rhodobacter, Salmonella, Shigella, Sphingomonas* and *Vibrio*.

* * * * *